(12) United States Patent
Akhavan-Tafti et al.

(10) Patent No.: US 8,367,842 B2
(45) Date of Patent: Feb. 5, 2013

(54) FLUORESCENT DYES AND USES THEREOF

(75) Inventors: Hashem Akhavan-Tafti, Howell, MI (US); Renuka De Silva, Northville, MI (US); Guoping Wang, Novi, MI (US); Robert A. Eickholt, Troy, MI (US); Ravinder K. Gupta, Pembroke Pines, FL (US); Lakshmi S. Kaanumalle, Schenectady, NY (US)

(73) Assignee: Beckman Coulter, Inc., Brea, CA (US)

( * ) Notice: Subject to any disclaimer, the term of this patent is extended or adjusted under 35 U.S.C. 154(b) by 167 days.

(21) Appl. No.: 12/836,747

(22) Filed: Jul. 15, 2010

(65) Prior Publication Data

US 2011/0014599 A1    Jan. 20, 2011

Related U.S. Application Data

(60) Provisional application No. 61/225,985, filed on Jul. 16, 2009.

(51) Int. Cl.
*C07D 277/62* (2006.01)
(52) U.S. Cl. ..................................... 548/178
(58) Field of Classification Search ............... None
See application file for complete search history.

(56) References Cited

U.S. PATENT DOCUMENTS

| 5,098,828 A | 3/1992 | Geiger |
| 5,424,440 A | 6/1995 | Klem et al. |

FOREIGN PATENT DOCUMENTS

| WO | 9903849 A1 | 1/1999 |
| WO | 2006130551 A2 | 12/2006 |

OTHER PUBLICATIONS

Bagley, MC. et al., J. Am. Chem. Soc., 122, 3301-3313 (2000).
Hermanson, Greg T., Bioconjugate Techniques, 1996 Edition Academic Press, Chapter 8, pp. 298-362.
Ji, T.H., "Bifunctional Reagents," Methods in Enzymology, 91, 580-609 (1983).
Kricka, LJ., Analytical Biochemistry, 175, 14-21 (1988).
Kricka, L.J., Ligand-Binder Assays, Marcel Dekker, Inc., New York, 1985, pp. 18-20, Table 2.2.
Bhatacharya, Bioconjug Chem. Jun. 2008; 19(6): 1186-1193.
Panchuk, Nataliya, J.of Histochemistry & Cytochemistry, vol. 47(9): 1179-1188, (1999).
White E H et al: "The chemi and bioluminescence of firefly luciferin: An efficient chemical production of electronically excited states" Bioorganic Chemistry, Academic Press Inc., New York, NY US, vol. 1, No. 1-2 Sep. 1, 1971, pp. 92-122, XP024022941, ISSN: 0045-2068.

*Primary Examiner* — Kamal Saeed
*Assistant Examiner* — Nyeemah A Grazier
(74) *Attorney, Agent, or Firm* — Hema Pande; Richard S. Handley

(57) ABSTRACT

The present invention provides fluorescent dyes that are based on firefly luciferin structure. These dyes are optimally excited at shorter wavelengths and have Stokes shift of at least 50 nm. The fluorescent dyes of the invention are useful for preparation of dye-conjugates, which can be used in detection of an analyte in a sample.

13 Claims, 5 Drawing Sheets

FLUORESCENT DYES AND USES THEREOF

This application claims priority to U.S. Provisional Application Ser. No. 61/225,985, filed Jul. 16, 2009, the contents of which are hereby incorporated by reference in their entirety into this application.

FIELD OF THE INVENTION

The present invention relates to fluorescent dyes, more specifically, ultraviolet excitable fluorescent dye compositions, compounds and conjugates, as well as method of using and making the same.

BACKGROUND OF THE INVENTION

Fluorescent dyes are widely used for labeling, detecting, and/or quantifying components in a sample. The various approaches used for such detection and/or quantification include fluorescence microscopy, fluorescence immunoassay, flow cytometric analysis of cells, and various other applications. In general, for many applications that utilize fluorescent dyes as detection tools, it is necessary to conjugate the fluorescent dye with a ligand such as a protein, antibody, enzyme, nucleotide, nucleic acid, and other biological and non-biological molecules to make a dye-labeled ligand. The dye-labeled ligand is an important reagent that confers specificity for a subsequent biochemical interaction in which the fluorescent dye provides a method for detection and/or quantification of the interaction.

The choice in fluorescent dyes is particularly important in applications that utilize multiplex, multicolor analysis, such as fluorescence microscopy, fluorescence immunoassay, flow cytometry, and various other applications. Notably, certain detection applications require an ultraviolet excitable fluorophore having a specific excitation range.

Specifically, there is a need for a fluorescent dye that can be efficiently excited by the 405 nm violet laser in multi-color flow cytometry instruments. The target dye for such applications should essentially have the following features: 1) a maximum in its excitation spectrum near 405 nm, 2) a strong spectrally resolvable emission maximum, 3) a large Stokes' shift, preferably, at least 50 nm, and 4) the ability of the fluorescent dye to couple to a biomolecule through a reactive group. Heretofore, there is a shortage of ultraviolet excitable fluorophores that can be conjugated to different ligands to provide dye-labeled reagents having optically and electronically separable fluorescence spectral properties.

The fluorescent dyes of the invention are structurally similar to firefly luciferin compounds. Such compounds have been previously used as chemiluminescent reagents whereby light is generated by the oxidative catalysis of luciferin. Luciferin, a substrate for the enzyme luciferase, is oxidized in the presence of luciferase to produce oxyluciferin and energy which is released in the form of light. For these types of assays, the luciferase-luciferin reaction provides the basis for simple, rapid, and sensitive assays for a wide range of substances (Karicka, L J., Analytical Biochemistry, 175, 14-21 (1988)).

While such chemiluminescent dyes based on the structure of firefly luciferin have gained widespread use, such use does not evidence the capability of compounds having a structure similar to that of firefly luciferin to function as fluorescent dyes excitable within a specific part of the ultraviolet spectrum. Such ultraviolet excitable fluorescent dyes are particularly advantageous for a wide range of applications, including without limitation, applications that utilize multiplex, multicolor fluorescence analysis.

SUMMARY OF THE INVENTION

The present invention relates to novel ultraviolet excitable fluorescent dyes based generally on the firefly Luciferin structure, compositions comprising the same, intermediates thereof and methods of their use.

In one aspect, compositions of fluorescent dyes having the following general formula (I) are provided:

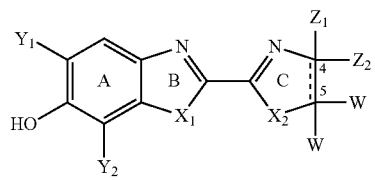

wherein
$X_1$ and $X_2$ are independently S or O;
$Y_1$ and $Y_2$ are independently halogen, alkyl, haloalkyl, alkoxy, or alkenyl, or one of
$Y_1$ or $Y_2$ is H, and the other is a haloalkyl group;
wherein each W is independently H or alkyl;
$Z_1$ is H or alkyl;
wherein $Z_1$ and one of the W groups may be absent and, if absent, are replaced with an additional bond between $C_4$ and $C_5$ in ring C, which is indicated by a dotted line;
$Z_2$ comprises a labeling substituent of the formula -L-RG, wherein L is a bond or a linking group; and
RG is a reactive group which enables the fluorescent dye to be bound to another molecule.

In another aspect, synthetic intermediates for synthesizing the fluorescent dyes of the invention are provided. In one embodiment, the synthetic intermediates are represented by the general formula.

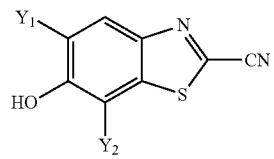

wherein
$Y_1$ and $Y_2$ are independently, halogen, alkyl, haloalkyl, alkoxy, or alkenyl, or one of $Y_1$ or $Y_2$ is H, and the other is a haloalkyl group.

In another aspect, dye-conjugates comprising fluorescent dyes conjugated to biomolecules are provided.

In another aspect, methods of using fluorescent dyes and dye-conjugates to locate or detect the presence or interaction of analytes or ligands in a sample are provided. In specific embodiments, methods of using the dye-conjugates for detecting the presence of complementary biomolecules that bind to the dye-conjugates are provided.

In other embodiments reagents and kits comprising the fluorescent dyes, dye intermediates, or dye-conjugates are provided for use in detecting the presence of complementary biomolecules that bind to the dye-conjugates of the invention.

DETAILED DESCRIPTION OF INVENTION

Definitions

Figure 1:
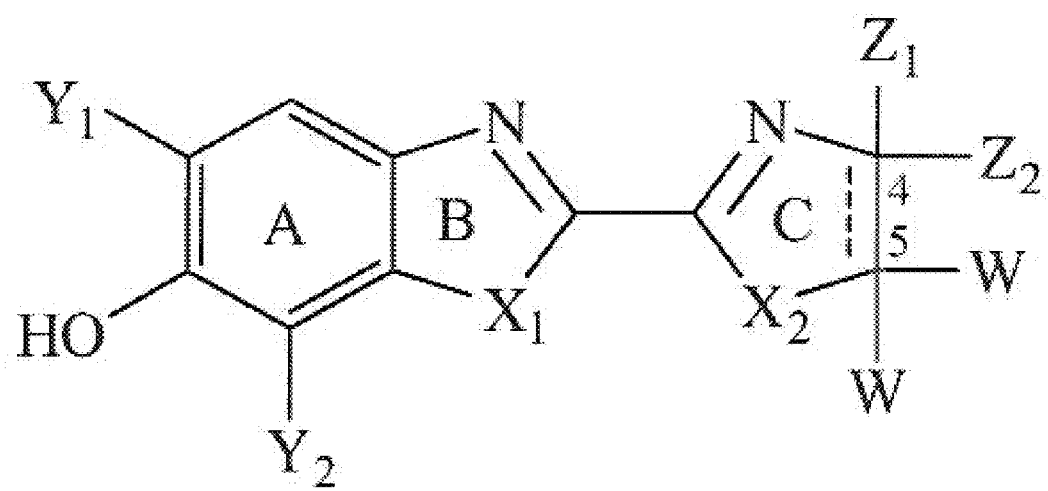
FIG. 1 depicts a general structure of ultraviolet excitable fluorescent dyes of the invention.

All scientific and technical terms used in this application have meanings commonly used in the art unless otherwise specified. As used in this application, the following words or phrases have the meanings specified.

As used herein, the term "activated ester" means an ester which spontaneously reacts with an amino group. Activated esters generally have the formula —COR, where R is a good leaving group. Activated esters include, but are not limited to, succinimidyloxy ($-OC_6H_4O_2$) also known as N-hydroxy-succinimide ester, sulfosuccinimdyloxy ($-OC_6H_3O_2-SO_3H$), -1-oxybenzotriazolyl ($-OC_6H_4N_3$).

As used herein, the term "alkyl" means a branched, straight chain or cyclic hydrocarbon group containing from 1-20 carbons. The term "alkyl" includes a "lower alkyl" group which typically contains up to 8 carbons.

As used herein, the term "alkenyl" means a branched, straight chain or cyclic hydrocarbon group containing at least one C—C double bond and containing from 2-20 carbons. The term "alkenyl" includes a "lower alkenyl" group which typically contains up to 8 carbons.

As used herein, the term "alkynyl" means a branched or straight chain hydrocarbon group containing at least one C—C triple bond and containing from 2-20 carbons. The term "alkynyl" includes a "lower alkynyl" group which typically contains up to 8 carbons.

As used herein, the term "aryl" means an aromatic ring-containing group containing 1-5 carbocyclic aromatic rings, which can be substituted with 1 or more substituents other than H.

As used herein, the term "analyte" means a substance the presence or amount of which is to be measured in a sample by an assay. The analyte may include a reactive group, e.g., a group through which a dye of the invention can be conjugated to the analyte. Analytes include organic and biological molecules to which a specific binding partner having a specific binding affinity exists. Exemplary analytes include, without limitation, single stranded or double stranded DNA, RNA, DNA-RNA complexes, oligonucleotides, antibodies, antibody fragments, antibody-DNA chimeras, antigens, haptens, proteins, lectins, avidin, streptavidin and biotin. Other exemplary analytes also include drugs and hormones.

As used herein, the term "conjugated molecule" or "CM" means a biological or non-biological component that is associated with at least one dye of the present invention. Such components include without limitations antigens, antibodies, carbohydrates (e.g., mono-, oligo-, and poly-saccharides), proteins, peptides, haptens, nucleosides, nucleotides, oligonucleotides, nucleic acids, polymers, virus, microorganism, or cell or cellular components. "Conjugated molecule" also includes solid supports (e.g., synthesis support, chromatographic support, membrane, or beads).

As used herein, the term "fluorescent dye" means a compound that absorbs light in the ultraviolet and violet regions of the electromagnetic spectrum, and reemits light in the blue region to produce a detectable signal. "Fluorescent Dye" also includes fluorescent compounds having a chemically reactive group that facilitates attachment of dye to a conjugate molecule.

As used herein the term "dye-conjugate" means a molecule in which a fluorescent dye is associated with a biological or non-biological component. Such biological or non-biological component is also referred to as "conjugated molecule". In one embodiment, the association of a fluorescent dye to a conjugated molecule is via a covalent linkage. The examples of the dye-conjugates include, but are not limited to, conjugates of antigens, antibodies, carbohydrates, proteins, peptides, haptens, nucleosides, nucleotides, oligonucleotides, nucleic acids, polymers, solid supports (e.g., synthesis supports, chromatographic supports, membranes, or beads), virus, microorganism, or cell or cellular components.

As used herein the term "fluorophore" means a molecule which is capable of absorbing energy at a wavelength range and releasing energy at a wavelength range other than the absorbance range. The term "excitation wavelength" means the range of wavelengths at which a fluorophore absorbs energy. The term "emission wavelength" means the range of wavelengths that the fluorophore releases energy or fluoresces.

As used herein the term "halogen" means fluorine, chlorine, bromine or iodine atoms. Similarly, the term "halo" means fluoro, chloro, bromo, or iodo group.

As used herein the term "haloalkyl" means an alkyl group in which one or more hydrogen atoms is replaced by one or more halogen atoms. In one embodiment, the haloalkyl can be substituted with 1, 2, or 3 halo groups. The term haloalkyl also includes perfluoro-alkyl groups. Examples of haloalkyls include trifluoromethyl, trichloromethyl, pentafluoroethyl, pentachloroethyl, and the like.

As used herein the term "linking group" or "L" means a group for linking the dye to the reactive group or RG. The linking group can be a bond, an atom, or another divalent or polyvalent group. The linking group can comprise a straight or branched chain of atoms some of which can be part of a ring structure. The linking group usually contains from 1 to about 50 non-hydrogen atoms, more usually from 1 to about 30 non-hydrogen atoms. Atoms comprising the chain are selected from C, O, N, S, P, Si, B, and Se atoms, preferably from C, O, N, P and S atoms that covalently link the fluorescent dye to another moiety such as a chemically reactive group. Halogen atoms can be present as substituents on the chain or ring. Typical functional groups comprising the linking substituent include alkene, alkylene, arylene, alkenylene, ether, peroxide, carbonyl as a ketone, ester, carbonate ester, thioester, or amide group, amine, amidine, carbamate, urea, imine, imide, imidate, carbodiimide, hydrazine, diazo, phosphodiester, phosphotriester, phosphonate ester, thioether, disulfide, sulfoxide, sulfone, sulfonate ester, sulfate ester, and thiourea groups. Examples of linking groups include substituted or unsubstituted polymethylene, arylene, alkylarylene, arylenealkyl, or arylthio.

One linking group according to the present invention for linking dye to a reactive group has the general structure $R_1C(O)R_2$, where $R_1$ is a bond or $C_{1-10}$ methylene $(CH_2)_n$ attached to the dye, C(O) is a carbonyl group, and $R_2$ is OH or a bond attaching the carbonyl group to a reactive group RG. Examples of this linking group include:

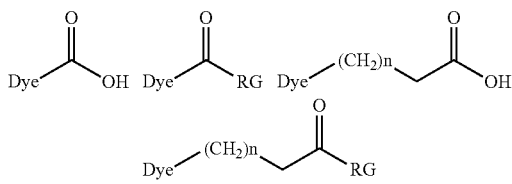

In another embodiment, illustrated below, the linking group has the general structure $R_1C(O)A_1R_3C(O)R_2$, where $R_1$ is a bond or $C_{1-10}$ methylene as described above, $A_1$ is either NH, S or O, $R_3$ is an alkenyl$(CH_2)n$, a five or a six membered ring having at least one unsaturated bond, or a combination of $C_{1-10}$ methylene $(CH_2)n$ and a five or six member ring, $R_2$ is OH or a bond attaching the terminal carbonyl group to a reactive group RG. Examples of this linking group include:

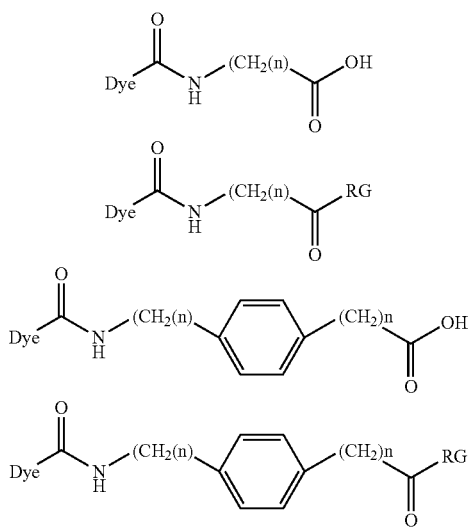

As used herein, the term "reactive group" or "RG" is an atom or group whose presence facilitates bonding to another molecule by covalent attachment or physical forces. Selected examples of reactive groups are shown in Table 1. In some embodiments, attachment of a fluorescent compound of the present invention to another compound will involve loss of one or more atoms from the reactive group for example when the reactive group is a leaving group such as a halogen atom or a tosylate group and the fluorescent labeling compound is covalently attached to another compound by a nucleophilic displacement reaction. In other embodiments, attachment of a fluorescent labeling compound to another compound by covalent bond formation will involve reorganization of bonds within the reactive group as occurs in an addition reaction such as a Michael addition or a cycloaddition reaction such as the Diels-Alder reaction or when the reactive group is an isocyanate or isothiocyanate group. In still other embodiments, attachment will not involve covalent bond formation, but rather physical forces in which case the reactive group remains unaltered. By physical forces is meant attractive forces such as hydrogen bonding, electrostatic or ionic attraction, hydrophobic attraction such as base stacking, and specific affinity interactions such as biotin-streptavidin, antigen-antibody and nucleotide-nucleotide interactions.

TABLE 1

Reactive Groups for Chemical Binding of Dyes to Conjugated Molecules

| REACTIVE GROUP (RG)(attached to reactive dye) | FUNCTIONAL GROUP (attached to conjugated molecule) |
| --- | --- |
| carboxylic acid | amine |
| carboxyl ester | amine |
| activated ester | amine |
| acid anhydride | amine |
| acid halide | amine |
| acyl azide | amine |
| aldehyde | amine |
| chloroformate | amine |
| isocyanate | amine |
| isothiocyanate | amine |
| sulfonyl halide | Amine/hydroxyl |
| alkyl halide | thiol |
| Alkyl sulfonate | thiol |
| aziridine | thiol |
| haloacetamide | thiol |
| maleimide | thiols |
| amine | Carboxylic acid |
| carbodiimide | Carboxylic acid |
| diazoalkane | Carboxylic acid |
| acyl halide | hydroxyl |
| halotriazine | hydroxyl |
| hydrazine/hydrazide | hydroxyl |
| phosphoramidites | alcohols |

When the reactive group is a moiety, such as a carboxylic acid or an activated ester of a carboxylic acid, the reactive dye is particularly useful for preparing dye conjugates with molecules containing one or more amino groups, such as proteins, peptides, nucleotides, oligonucleotides, or haptens. Where the reactive group is a maleimide or haloacetamide, the reactive dye is particularly useful for conjugation with thiol-containing molecules. Where the reactive group is a hydrazide, the reactive dye is particularly useful for conjugation to periodate-oxidized carbohydrates and glycoproteins.

In one embodiment, reactive groups include carboxylic acid, succinimidyl ester of a carboxylic acid, isothiocyanate, haloacetamide, hydrazine, aliphatic amine, and maleimide groups. Methods to prepare each of these reactive groups are well known in the art and their application for a particular purpose is within the ability of one having skill in the art.

Bifunctional coupling reagents can also be used to couple labels to organic and biological molecules with moderately reactive groups (see L. J. Kricka, Ligand-Binder Assays, Marcel Dekker, Inc., New York, 1985, pp. 18-20, Table 2.2 and T. H Ji, "Bifunctional Reagents," Methods in Enzymology, 91, 580-609 (1983)). There are two types of bifunctional reagents, those which become incorporated into the final structure and those which do not and serve only to couple the two reactants.

As used herein, the term "sample" means a fluid containing or suspected of containing one or more analytes to be assayed. Typical samples which are analyzed utilizing fluorescent dyes are biological samples including body fluids such as blood, plasma, serum, urine, semen, saliva, cell lysates, tissue extracts and the like. The sample can also include diluents, buffers, detergents, contaminants, and the other such components that are usually present in a body fluid.

As used herein the term "specific binding pair" means two substances which exhibit a mutual binding affinity. Examples include antigen-antibody, hapten-antibody, antibody-antibody pairs, complementary oligonucleotides or polynucleotides, avidin-biotin, streptavidin-biotin, enzyme-substrate, hormone-hormone receptor, lectin-carbohydrate, IgG-protein A, IgG-protein G, nucleic acid-nucleic acid binding protein, and nucleic acid-anti-nucleic acid antibody (Table 2).

TABLE 2

REPRESENTATIVE SPECIFIC BINDING PAIRS

| | |
|---|---|
| antigen | antibody |
| hapten | antibody |
| biotin | avidin or strepavidin |
| carbohydrate | lectin or carbohydrate receptor |
| DNA | complementary strand DNA |
| RNA | complementary strand RNA |
| drug | drug receptor |
| IgG | protein A/protein G |
| substrate | enzyme |
| Protein/peptide | protein/peptide receptor |
| hormone | hormone receptor |
| Nucleic acids | Anti-nucleic acid antibody |

As used herein, the term "substituted" means replacement of at least one hydrogen atom on a group by another atom or a group having 1 to 50 atoms selected from C, O, N, S, P, Si, F, Cl, Br, I. In references to substituted groups, it is intended that multiple points of substitution can be present.

Compositions of Invention

The invention provides a class of fluorescent dyes that are based on the structure of firefly luciferin, and possess certain functional advantages. For example, the fluorescent dyes of the invention are adapted for excitation at shorter wavelengths (between 340 and 450 nm), have emission maxima usually between 500 and 550 nm wavelengths, narrow emission bandwidth, a large Stokes shift of at least about 50 nm, and other favorable fluorescent properties.

The fluorescent dyes of the present invention are particularly useful with violet 405 nm lasers. Compared to existing violet laser excitable dyes (e.g., Pacific Orange), the fluorescent dyes of the invention, despite having comparable absorptivity, show surprisingly and unexpectedly brighter fluorescence. The fluorescent dyes of the invention are well adapted for coupling to a conjugated molecule through a reactive group. In addition, the dye-conjugates of the invention, in particular, the protein conjugates, exhibit bright fluorescence even at a relatively high degree of dye substitution. These properties make the dyes of the invention particularly well-suited for multicolor, multiplexing application.

The fluorescent dyes of the general formula are provided:

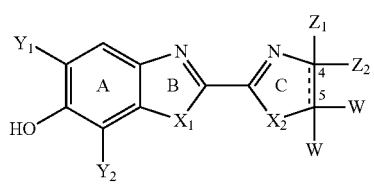

(I)

wherein $X_1$ and $X_2$ are independently S or O;

$Y_1$ and $Y_2$ are independently halogen, alkyl, haloalkyl, alkoxy, or alkenyl, or one of $Y_1$ or $Y_2$ is H, and the other is a haloalkyl group;

wherein each W is independently H or alkyl;

$Z_1$ is H or alkyl;

wherein $Z_1$ and one of the W groups may be absent and, if absent, are replaced with an additional bond between $C_4$ and $C_5$ in ring C, which is indicated by a dotted line;

$Z_2$ comprises a labeling substituent of the formula -L-RG, wherein L is a bond or a linking group which connects the dye to a reactive group RG, wherein the linking group can comprise a covalent linkage comprising 1-50 non-hydrogen atoms selected from C, N, O, S, P and halogen atoms and is composed of any combination single, double, triple, or aromatic carbon-carbon bonds, carbon-oxygen bonds, carbon-sulfur bonds, carbon-nitrogen bonds, and nitrogen-nitrogen bonds; and wherein RG includes a carboxylic acid, an activated ester of a carboxylic acid, acid anhydride, acid chloride, acyl azide, an acyl halide, aldehyde, chloroformate, amine, hydroxy, hydrazine, isocyanate, isothiocyanate, sulfonyl halide, tosyl, maleimide, N-hydroxy-succinimide ester, aziridine, imine, and disulfide groups.

In one embodiment of the fluorescent dye of formula (I), $X_1$ and $X_2$ are S having the formula:

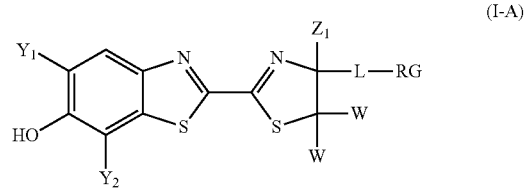

(I-A)

wherein $Y_1$ and $Y_2$ are independently halogen, alkyl, haloalkyl, alkoxy, or alkenyl, or one of $Y_1$ or $Y_2$ is H, and the other is a haloalkyl group;

$Z_1$ is H or alkyl;

wherein each W is independently H or alkyl;

in L-RG, L is a bond or a linking group which connects the dye to a reactive group RG, wherein the linking group can comprise a covalent linkage comprising 1-50 non-hydrogen atoms selected from C, N, O, S, P and halogen atoms and is composed of any combination single, double, triple, or aromatic carbon-carbon bonds, carbon-oxygen bonds, carbon-sulfur bonds, carbon-nitrogen bonds, and nitrogen-nitrogen bonds; and wherein RG can comprise a carboxylic acid, an activated ester of a carboxylic acid, acid anhydride, acid chloride, acyl azide, an acyl halide, aldehyde, chloroformate, amine, hydroxy, hydrazine, isocyanate, isothiocyanate, sulfonyl halide, tosyl, maleimide, N-hydroxy-succinimide ester, aziridine, imine, and disulfide groups.

Selected embodiments of the dyes of formula (I-A) are illustrated in Table 3

TABLE 3

| Dye | X1 | X2 | Y1 | Y2 | ZI | W | L | RG |
|---|---|---|---|---|---|---|---|---|
| I-A-1 | S | S | H | H | H | Me | C(O) | OH |
| I-A-2 | S | S | H | H | H | Me | C(O) | NHS |

TABLE 3-continued

| Dye | X1 | X2 | Y1 | Y2 | ZI | W | L | RG |
|---|---|---|---|---|---|---|---|---|
| I-A-3 | S | S | H | H | H | Me | C(O) | NHBSA |
| I-A-4 | S | S | Cl | H | H | Me | C(O) | OH |
| I-A-5 | S | S | H | Cl | H | Me | C(O) | OH |
| I-A-6 | S | S | Cl | Cl | H | Me | C(O) | OH |
| I-A-7 (Dye1) | S | S | Cl | Cl | H | Me | C(O) | NHS |
| I-A-8 | S | S | Cl | Cl | H | Me | C(O) | NHBSA |
| I-A-9 (Dye2) | S | S | Cl | Cl | H | Me | C(O)NH(CH$_2$)$_5$C(O) | NHS |
| I-A-10 | S | S | Cl | Cl | H | Me | C(O)NH(CH$_2$)$_5$C(O) | NHBSA |
| I-A-11 | S | S | Cl | Cl | H | Me | C(O)NH(CH$_2$)$_2$NHCSNHPh | NCS |
| I-A-12 | S | S | Cl | Cl | H | Me | C(O)NH(CH$_2$)$_2$NHCSNHPh | NHCSNHBSA |
| I-A-13 | S | S | F | F | H | Me | C(O) | OH |
| I-A-14 (Dye3) | S | S | F | F | H | Me | C(O) | NHS |
| I-A-15 | S | S | F | F | H | Me | C(O) | NHBSA |
| I-A-16 | S | S | Me | Me | H | Me | C(O) | OH |
| I-A-17 | S | S | Me | H | H | Me | C(O) | OH |
| I-A-18 | S | S | CF3 | H | H | Me | C(O) | OH |
| I-A-19 (Dye7) | S | S | CF3 | H | H | Me | C(O) | NHS |
| I-A-20 | O | S | H | H | H | Me | C(O) | OH |
| I-A-21 | S | S | F | F | H | Me | C(O)NH(CH$_2$)$_2$C(O) | OH |
| I-A-22 (Dye5) | S | S | F | F | H | Me | C(O)NH(CH$_2$)$_2$C(O) | NHS |
| I-A-23 | S | S | F | F | H | Me | C(O)NHCH$_2$C(O) | OH |
| I-A-24 | S | S | Cl | Cl | H | Me | C(O)NH(CH$_2$)$_2$C(O) | OH |
| I-A-25 | S | O | F | F | H | H | C(O) | OH |
| I-A-26 | S | S | Cl | H | H | H | C(O) | OH |
| I-A-27 | S | S | H | Cl | H | H | C(O) | OH |
| I-A-28 | S | S | Cl | Cl | H | H | C(O) | OH |
| I-A-27 | S | S | F | F | Me | H | C(O) | OH |
| I-A-29 (Dye4) | S | S | F | F | Me | H | C(O) | NHS |
| I-A-30 | S | S | F | F | H | H | C(O) | OH |
| I-A-31 | S | S | F | F | H | H | C(O) | NHS |
| I-A-32 | S | S | H | H | H | H | C(O) | OH |
| I-A-33 | S | S | F | F | H | H | (CH2)$_2$C(O) | OH |
| I-A-34 (Dye6) | S | S | F | F | H | H | (CH2)$_2$C(O) | NHS |

In other embodiments, the fluorescent dyes have the following formula:

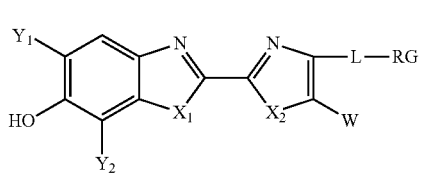

(I-B)

wherein
$X_1$ and $X_2$ are independently S or O;
$Y_1$ and $Y_2$ are independently halogen, alkyl, haloalkyl, alkoxy, or alkenyl;
or
one of $Y_1$ or $Y_2$ is H, and the other is a haloalkyl group;
W is H or alkyl;
L is a bond or a linking group which connects the dye to a reactive group RG,
wherein the linking group can comprise a covalent linkage comprising 1-50 non-hydrogen atoms selected from C, N, O, S, P and halogen atoms and is composed of any combination single, double, triple, or aromatic carbon-carbon bonds, carbon-oxygen bonds, carbon-sulfur bonds, carbon-nitrogen bonds, and nitrogen-nitrogen bonds; and
wherein RG can comprise a carboxylic acid, an activated ester of a carboxylic acid, acid anhydride, acid chloride, acyl azide, an acyl halide, aldehyde, chloroformate, amine, hydroxy, hydrazine, isocyanate, isothiocyanate, sulfonyl halide, tosyl, maleimide, N-hydroxy-succinimide ester, aziridine, imine, and disulfide groups.

In one embodiment of the fluorescent dye of formula (I-B), X1 and X2 are S, as provided in formula:

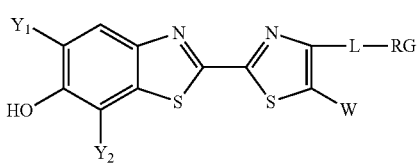

wherein,
$Y_1$ and $Y_2$ are independently halogen, alkyl, haloalkyl, alkoxy, or alkenyl
or
one of $Y_1$ or $Y_2$ is H, and the other is a haloalkyl;
W is H or alkyl;
L is a bond or a linking group, wherein the linking group comprises a covalent linkage comprising 1-50 non-hydrogen atoms selected from C, N, O, S, P and halogen atoms and is composed of any combination single, double, triple, or aromatic carbon-carbon bonds, carbon-oxygen bonds, carbon-sulfur bonds, carbon-nitrogen bonds, and nitrogen-nitrogen bonds; and
RG is a reactive group, wherein RG can comprise a carboxylic acid, an activated ester of a carboxylic acid, acid anhydride, acid chloride, acyl azide, an acyl halide, aldehyde, chloroformate, amine, hydroxy, hydrazine, isocyanate, isothiocyanate, sulfonyl halide, tosyl, maleimide, N-hydroxy-succinimide ester, aziridine, imine, and disulfide groups.

Selected embodiments of dyes of formula (I-B) are illustrated in Table 4.

TABLE 4

| Dye | X1 | X2 | Y1 | Y2 | W | L | RG |
|---|---|---|---|---|---|---|---|
| I-B-1 | S | S | Cl | Cl | H | C(O) | OH |
| I-B-2 | S | S | Cl | Cl | H | C(O) | NHS |
| I-B-3 | S | S | Cl | Cl | Me | C(O) | OH |
| I-B-4 | S | S | Cl | Cl | Me | C(O) | NHS |
| I-B-5 | S | S | F | F | Me | C(O) | OH |
| I-B-6 | S | S | F | F | Me | C(O) | NHS |
| I-B-7 | S | S | F | F | H | C(O) | OH |
| I-B-8 | S | S | F | F | H | C(O) | NHS |

The invention further provides synthetic intermediate compounds that may be used for synthesizing the fluorescent dyes of the invention. In one embodiment, the intermediate compounds are represented by the general formula (II):

(II)

wherein
$Y_1$ and $Y_2$ are independently halogen, alkyl, haloalkyl, alkoxy, or alkenyl
or
one of Y1 or $Y_2$ is H, and the other is a haloalkyl group.

In another embodiment, the intermediate compounds are represented by the general formula (III):

(III)

wherein
$X_2$ is S or O;
wherein each W is independently H or alkyl;
$Z_1$ is H or alkyl; and
LH is OH or $NH(CH_2)nCOOH$ (n is 1-10).

The fluorescent dyes of the invention may be covalently or non-covalently associated with one or more conjugated molecules "CM". Covalent association may occur through various mechanisms, including attachment of a conjugated molecule CM to the fluorescent dye via a linking group L as described above, and may involve a covalent linkage.

Where the dye is associated non-covalently with one or more molecules, the association may occur through various mechanisms, including incorporation of the dye or synthetic intermediate compound into or onto a solid or semisolid matrix, such as a bead or a surface, or by nonspecific interactions, such as hydrogen bonding, ionic bonding, or hydrophobic interactions (such as Van der Waals forces). The associated molecules may be selected from the group consisting of polypeptides, polynucleotides, polysaccharides, beads, microplate well surfaces, metal surfaces, semiconductor and non-conducting surfaces, nano-particles, and other solid surfaces.

The associated or conjugated molecule may be associated with or conjugated to more than one fluorescent dye, which may be the same or different. Generally, methods for the preparation of dye-conjugates of biological substances are well-known in the art. See, for example, (Greg T. Hermanson, Bioconjugate Techniques, 1996 Edition Academic Press, Chapter 8, pages 298-362; Nataliya Panchuk, et al. J. Histochemistry & Cytochemistry, 1179-1188 (1999); S Bhatacharya, et al Bioconjugate Chemistry, Volume 19, 1186-1193 (2008); B. Dworecki, et al http://www.piercenet.com/files/DyLight%20Poster%206-7-04.pdf). Typically, the association or conjugation of a fluorophore to a dye-conjugate imparts the spectral properties of the fluorophore to that molecule.

In one embodiment, a fluorescent dye of the invention is attached to a conjugated molecule CM via a covalent linkage, the dye-conjugate having the formula:

wherein
$X_1$ and $X_2$ are independently S or O;
$Y_1$ and $Y_2$ separately represent H, halogen, alkyl, haloalkyl, alkoxy, or alkenyl
wherein each W is independently H or alkyl;
$Z_1$ is H or alkyl;
wherein $Z_1$ and one of the W groups may be absent and, if absent, are replaced with an additional bond between $C_4$ and $C_5$ in ring C, which is indicated by a dotted line;
L is independently a bond or a linking group, wherein the linking group comprises a covalent linkage comprising 1-50 non-hydrogen atoms selected from C, N, O, S, P and halogen atoms and is composed of any combination single, double, triple, or aromatic carbon-carbon bonds, carbon-oxygen bonds, carbon-sulfur bonds, carbon-nitrogen bonds, and nitrogen-nitrogen bonds; and
wherein CM is a conjugated molecule.

Conjugated molecules CM that may be used for preparing dye-conjugates according to the present invention include, but are not limited to, amino acids, peptides, proteins, nucleosides, nucleotides, nucleic acids, carbohydrates, enzymes, lipids, non-biological polymers, cells, and cellular components. The molecules to be conjugated may be protected on one or more functional groups in order to facilitate the conjugation, or to insure subsequent reactivity.

Where the molecule is a peptide, the peptide may be a dipeptide or larger, and typically includes 5 to 50 amino acids. Where the conjugated molecule is a protein, it may be an enzyme, an antibody, catalytic antibody, kinase, lectin, glycoprotein, histone, albumin, lipoprotein, avidin, streptavidin, protein A, protein G, hormone, toxin, growth factor. Typically, the conjugated protein is an antibody, an antibody fragment, avidin, streptavidin, a lectin, or a growth factor.

The conjugated molecule may be a nucleic acid polymer, such as for example DNA oligonucleotides, RNA oligonucleotides (or hybrids thereof), or single-stranded, double-stranded, triple-stranded, or quadruple-stranded DNA, or single-stranded or double-stranded RNA. The conjugated molecule may also include carbohydrates that are polysaccharides, such as dextrans.

The associated or conjugated molecule may be a member of a specific binding pair, and therefore useful as a detection reagent for the complementary member of that specific binding pair. The dye-conjugate of a specific binding pair member may be useful for detecting and optionally quantifying the presence of the complementary specific binding pair member in a sample, by methods that are well known in the art.

Representative specific binding pairs may include without limitation ligands and receptors, and may include but are not limited to the following pairs: antigen-antibody, biotin-avidin, biotin-streptavidin, IgG-protein A, IgG-protein G, carbohydrate-lectin, enzyme-enzyme substrate; DNA-complementary strand DNA, and RNA-complementary strand RNA, hormone-hormone receptor (Table 2).

Methods of Preparing Fluorescent Dye Compounds

In one aspect of the invention a method is provided for preparing the fluorescent dyes of formula (I).

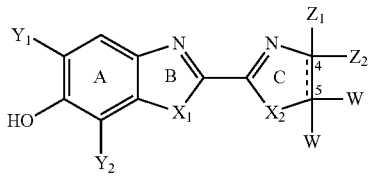

wherein $X_1$ and $X_2$ are independently S or O;

$Y_1$ and $Y_2$ separately represent H, halogen, alkyl, haloalkyl, alkoxy, or alkenyl wherein each W is independently H or alkyl;

$Z_1$ is H or alkyl;

wherein $Z_1$ and one of the W groups may be absent and, if absent, are replaced with an additional bond between $C_4$ and $C_5$ in ring C, which is indicated by a dotted line;

wherein $Z_2$ comprises a labeling substituent of the formula -L-RG, wherein L is independently a bond or a linking group, wherein the linking group comprises a covalent linkage comprising 1-50 non-hydrogen atoms selected from C, N, O, S, P and halogen atoms and is composed of any combination single, double, triple, or aromatic carbon-carbon bonds, carbon-oxygen bonds, carbon-sulfur bonds, carbon-nitrogen bonds, and nitrogen-nitrogen bonds; and wherein RG is a reactive group selected from a group consisting of a carboxylic acid, an activated ester of a carboxylic acid, acid anhydride, acid chloride, acyl azide, an acyl halide, aldehyde, chloroformate, amine, hydroxyl, hydrazine, isocyanate, isothiocyanate, sulfonyl halide, tosyl, maleimide, N-hydroxy-succinimide ester, aziridine, imine, and disulfide groups.

In one embodiment, the fluorescent dyes of the invention having the formula:

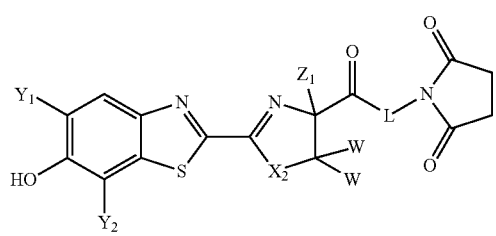

wherein $Y_1$ and $Y_2$ separately represent H, halogen, alkyl, haloalkyl, alkoxy, or alkenyl;

$X_2$ is S or O;

wherein each W is independently H or alkyl;

$Z_1$ is H or alkyl; and

Figure 2A:
FIG. 2A-2D depicts a synthesis scheme for luciferin derivatives.
Figure 2B:
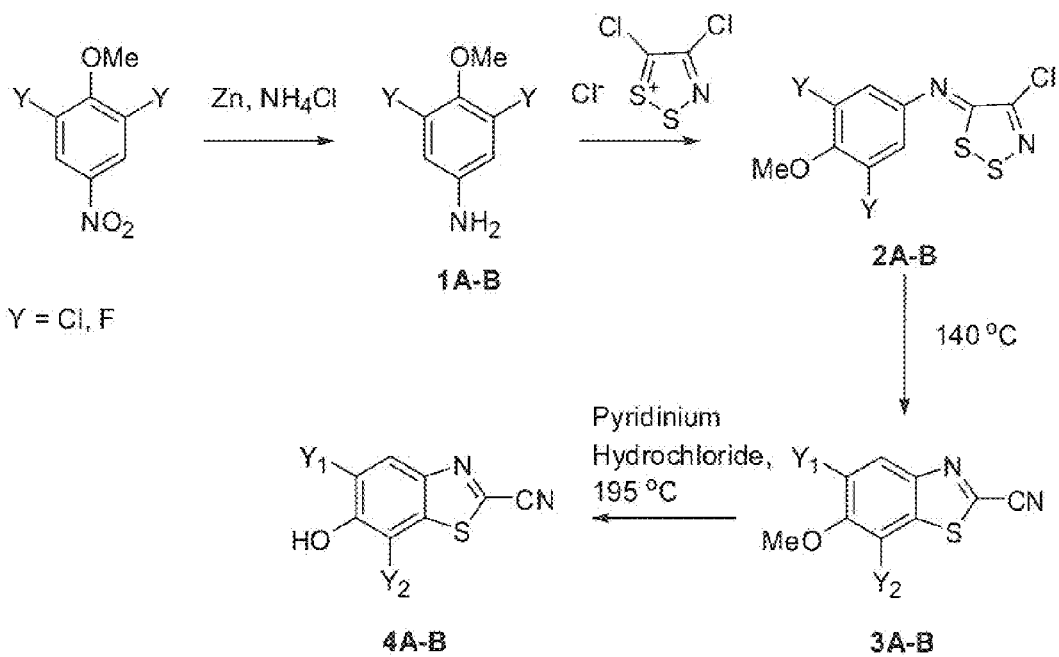
Figure 2C:
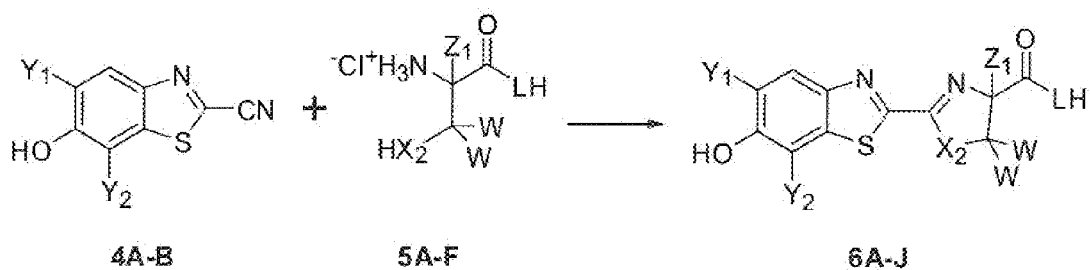
Figure 2D:
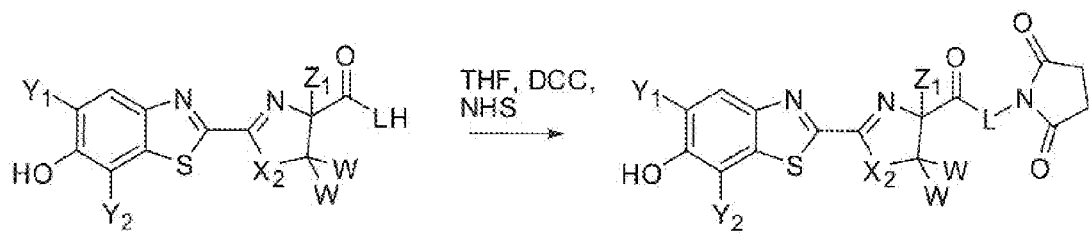

L is O or $NH(CH_2)nCOO$ (n is 1-10)

can be synthesized using the synthesis scheme illustrated in FIG. 2A-2D. The method includes the steps of:

(a) forming cyanobenzothiazole intermediate of the dye using the method shown in FIG. 2B having the formula:

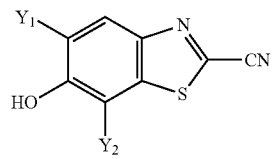

wherein $Y_1$ and $Y_2$ separately represent H, halogen, alkyl, haloalkyl, alkoxy, or alkenyl.

(b) forming a carboxyl derivative of the dye by reacting the cyanobenzothiazole intermediate with modified amino acid of formula:

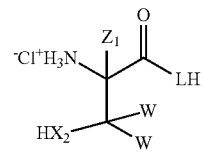

wherein $X_2$ is S or O;

wherein each W is independently H or alkyl;

$Z_1$ is H or alkyl; and

LH is OH or $NH(CH_2)nCOOH$ (n is 1-10).

to produce luciferin derivative of formula:

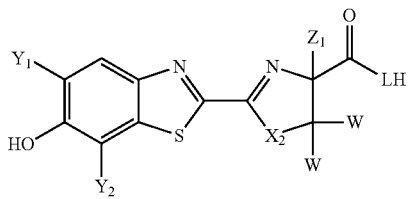

wherein $X_2$ is S or O;

$Y_1$ and $Y_2$ separately represent H, halogen, alkyl, haloalkyl, alkoxy, or alkenyl;

wherein each W is independently H or alkyl;

$Z_1$ is H or alkyl; and

LH is OH or $NH(CH_2)nCOOH$ (n is 1-10).

(c) replacing the hydroxyl function of the carboxyl group in LH with a reactive group.

Figure 3A:
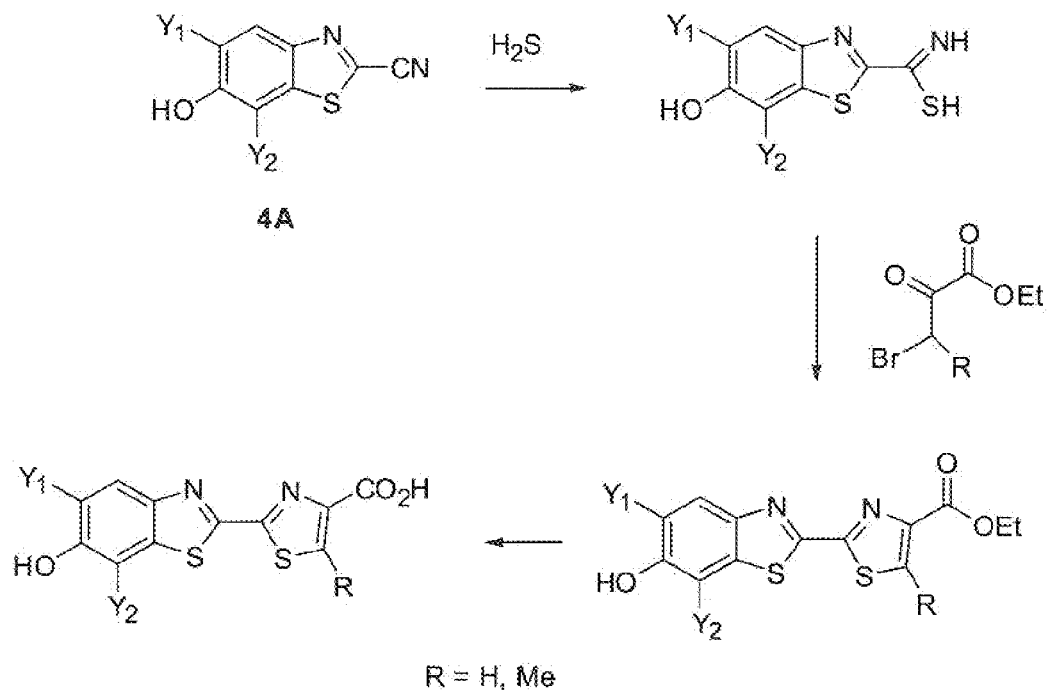
FIGS. 3A and 3B depict synthesis schemes for derivatives of dehydroluciferin acids.

In another embodiment, the fluorescent dyes of the invention having the formula:

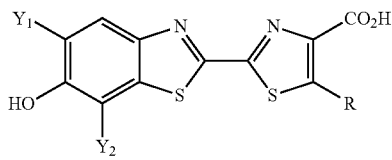

wherein
$Y_1$ and $Y_2$ separately represent H, halogen, alkyl, haloalkyl, alkoxy, or alkenyl; and
R is H or alkyl
are synthesized using the synthesis scheme illustrated in FIG. 3A.

Figure 3B:
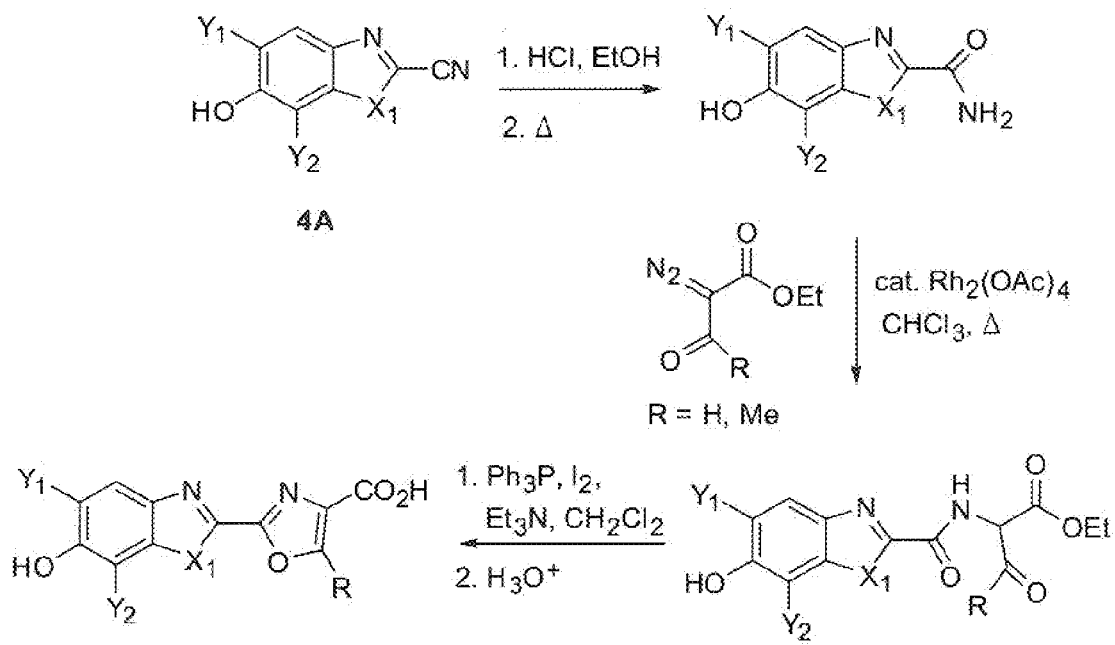

In another embodiment, the fluorescent dyes of the invention having the formula:

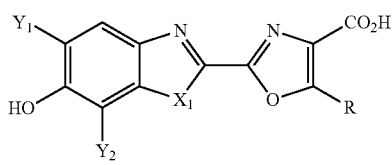

wherein
$Y_1$ and $Y_2$ separately represent H, halogen, alkyl, haloalkyl, alkoxy, or alkenyl; and
R is H or alkyl
can be synthesized using the synthesis scheme illustrated in FIG. 3B (Bagley, M C. et al., *J. Am. Chem. Soc.*, 122, 3301-3313 (2000).

In another aspect the invention provides methods for making dye-conjugates of invention. The method comprises mixing a fluorescent dye of the invention comprising a reactive group with a conjugated molecule. The conjugated molecule may be an amino acid, protein, peptide, antibody, antibody fragment, nucleoside, nucleotide, nucleic acid polymer. The conjugated molecule may include carbohydrates that are polysaccharides, such as dextrans. Typically, the conjugation of a fluorophore to a conjugated molecule imparts the spectral properties of the fluorophore to that molecule.

The methods for the preparation of dye-conjugates of are well-known in the art. For preparation of peptide or protein conjugates, the method typically comprises first dissolving the protein to be conjugated in aqueous buffer at about 1-10 mg/ml at room temperature or below (typically 4-25° C.). Borate or carbonate/bicarbonate buffers (pH about 8.0-9) are especially suitable for reaction with succinimidyl esters, phosphate buffers (pH about 4.0-8) for reaction with thiol-reactive functional groups, and carbonate or borate buffers (pH about 9.0-9.8) for reaction with isothiocyanates and dichlorotriazines. The appropriate reactive dye is dissolved in a nonaqueous solvent (usually DMSO or DMF) in an amount sufficient to give a suitable degree of conjugation and added to a solution of the protein to be conjugated. The appropriate amount of reactive dye to be used for any protein or other component is usually predetermined by experimentation in which variable amounts of the reactive dye are added to the protein to be conjugated. The reactive dye is usually used in 5-100 fold excess of the amount of protein to be conjugated. Following addition of the reactive compound to the component solution, the mixture is incubated for a suitable period (typically about 1 hour at room temperature to several hours on ice), the dye-conjugate is separated from unconjugated dye by gel filtration, dialysis, HPLC or other suitable methods. The dye-conjugate can be stored in solution or lyophilized, until tested in its desired application. This method is generally applicable for preparing dye-conjugates using antibodies, antibody fragments, avidins, lectins, enzymes, proteins A and G, cellular proteins, albumins, histones, growth factors, hormones, and other proteins.

Methods of Use

The present invention provides a method of detecting a complementary member of a specific binding pair in a sample, comprising mixing said sample with a dye-conjugate of the invention which specifically binds to the complementary member; and detecting the complex formed by said mixture to detect the complementary member. The methods of the invention may comprise using the fluorescent dyes, including reactive dyes and dye-conjugates of the invention for detection and/or quantitation of an analyte in a sample. In certain embodiments, the sample comprises heterogeneous mixtures of components, including intact cells, cell extracts, bacteria, viruses, organelles, and mixtures thereof. In other embodiments, the sample comprises a single component or homogeneous group of components, e.g. biological polymers such as amino acid polymers, nucleic acid polymers, carbohydrate polymers, or lipid membrane complexes.

In certain embodiments, the fluorescent dyes of the invention, including reactive dyes and dye-conjugates are used to stain or label an analyte in a sample so that the analyte can be identified or quantitated. For example, fluorescent dyes, including dye-conjugates of the invention may be used as a detectable tracer element in an assay for a target analyte, in a biological or non-biological fluid.

In other embodiments, the fluorescent dyes, including reactive dyes and dye-conjugates are used to detect a sample that comprises a ligand for which the conjugated molecule is a complementary member of a specific binding pair (e.g., Table 2). Thus, the ligand is one member and the conjugated molecule the other member of the specific binding pair. The fluorescent dyes, including the dye-conjugates are also used for identifying an interaction between a dye-conjugate and a complementary binding molecule.

In the first step of the method, the fluorescent dyes, including the reactive dyes and dye-conjugates of the invention are generally utilized by combining a dye of the invention as described above with the sample of interest under conditions selected to yield a detectable optical response. The dye-conjugate typically forms a covalent or non-covalent association or complex with an element of the sample, or is simply present within the bounds of the sample or portion of the sample. The sample is then illuminated at a wavelength selected to elicit the optical response. Typically, staining the sample is used to determine a specified characteristic of the sample by further comparing the optical response with a standard.

In one aspect of the invention, the dye-conjugate is a labeled protein, such as an antibody, antibody fragment, avidin or strepavidin, and the like. In this embodiment the dye-conjugate is used to detect a complementary specific binding pair which is typically, an antigen, a hapten or a biotin. Such dye-conjugates of the invention can be use for detection of an analyte in a sample, using a variety of applications. Primary applications include immunofluorescence, fluorescence in-situ hybridization (FISH), flow cytometry, labeling of receptors, and tracing of labeled cells. For certain detection methods e.g., those based on cytometry which inherently involve spatial separation/resolution of bound vs. unbound conjugate, it is not necessary to remove the unbound dye-conjugate from the analysis mixture. However, for other detection methods, e.g. immunoassays not involving spatial separation/resolution of bound vs. unbound conjugate, it may be necessary to remove the unbound dye-conjugate from the analysis mixture prior to detecting the optical response.

In another aspect, the fluorescent dyes and dye-conjugates of the invention may have utility as laser dyes. Since the dyes and dye-conjugates of the invention are excited by an ultraviolet or violet laser, these dyes and dye-conjugates are particularly useful for multiplex assays with other dyes that are excited at longer wavelengths. In one embodiment, these dyes and dye-conjugates are excited at about 350-405 nm and when used with dyes that are excited at longer wavelengths (e.g., 480 nm and longer), their emission spectra are distinguishable from the dyes that are excited at longer wavelengths.

In another aspect of the invention, the dye-conjugates of the invention can be used in a multi-color method for detecting one or more analytes in a sample. In one embodiment, the multiple dye-conjugates can be used to detect multiple analytes in a sample using a multi-color analysis. The method includes incubating the sample with a composition of the invention that includes multiple dye-conjugates, for example, a first dye-conjugate and second dye-conjugate. In this composition, the component of the first dye-conjugate is a binding partner for the first analyte and the component of the second dye-conjugate is a binding partner for the second analyte. The incubation continues under conditions appropriate to induce an interaction between the first analyte and the first dye-conjugate. During this incubation period, it is generally preferred that a similar interaction occurs between the second analyte and second dye-conjugate, however, it is within the scope of the invention to change the incubation conditions as necessary to drive the formation of a dye-conjugate-analyte complex between the second dye-conjugate and second analyte. Following the formation of at least the first dye-conjugate-analyte complex, the sample is illuminated with light of a wavelength appropriate to cause the complex to fluoresce, thereby detecting the first analyte. The second analyte is detected in a similar manner and may be detected simultaneously with the first analyte or by the sequential illumination of the sample with wavelengths appropriate to induce the fluorescence of each fluorescent dye-conjugate. In a particular aspect, the illumination and/or detection step comprises a flow cytometer.

Alternatively, the multiple dye-conjugates, preferably fluorescing at different wavelengths can be used to detect different features of an analyte. For example, a cell or epitopes of an analyte, can be labeled with different colored dye-conjugates, the target is detected and its identity is confirmed using the co-localization of each color on each target.

The dyes and dye-conjugates of the invention may be used for diagnostic applications. For example, the dyes and dye-conjugates of the invention may be useful for detecting the presence of a pathogenic organism (e.g., bacterial, viral, fungal) in a subject. Alternatively, presence of a particular analyte and/or amount of a particular analyte and/or variants of a particular analyte may be associated with a pathological condition in a subject. The dyes and dye-conjugates of the invention that bind to such analytes may have utility for determining the presence and/or amount of a particular analyte and/or its variants, thus diagnosing the presence and/or extent of a pathological condition.

Kits of Invention

One aspect of the present invention is the formulation of kits that facilitate the practice of various assays using any of the dyes of the invention, as described above. The kits of the invention typically comprise a fluorescent dye of the invention, either present as a chemically reactive label useful for preparing dye-conjugates, or present as a dye-conjugate where the conjugated molecule is a specific binding pair member. Selected conjugated molecules include without limitation, polymers of biological molecules (e.g. proteins, nucleic acids or carbohydrates). In specific embodiments, the dyes of the present invention listed in Tables 3 and 4 are particularly suited for the preparation of such a kit.

Preferably, the kits comprise one or more of fluorescent dyes listed in Table 5.

TABLE 5

| No. | Formula |
|---|---|
| Dye1 | |
| Dye2 | |

TABLE 5-continued

| No. | Formula |
|---|---|
| Dye3 | 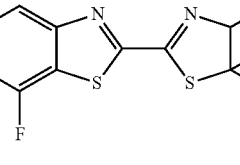 |
| Dye4 | 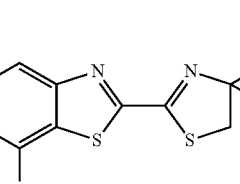 |
| Dye5 | 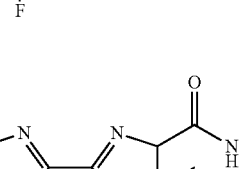 |
| Dye6 | 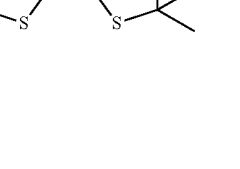 |
| Dye7 | 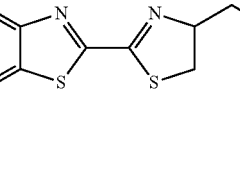 |

The kits can also comprise one or more of the dye-conjugates of Dye1, Dye2, Dye3, Dye4, Dye5, Dye6, or Dye7.

In an exemplary embodiment, the kit includes a reactive dye of the invention and instructions for conjugating the dye to a molecule possessing an appropriate functional group, and optionally for recovering the dye-conjugate.

In another exemplary embodiment, the kit includes instructions for performing an assay that detects an analyte or ligand in a sample. For example, in one embodiment, instructions are provided for detecting cell surface receptors, or an enzyme, or other ligands that can bind antibodies.

The kit optionally further comprises one or more buffering agents, typically present as an aqueous solution. The kits of the invention optionally further comprise additional detection reagents, a purification medium for purifying the resulting labeled molecules, fluorescent standards, enzymes, enzyme inhibitors, organic solvent, or instructions for carrying out a method of the invention.

The various embodiments of the invention are demonstrated further by the following illustrative examples. The examples are offered by way of illustration and are not intended to limit the scope of invention or claims in any manner.

Example 1

The following example provides a description of a general method for the synthesis of dihalo derivatives of firefly luciferin and their respective NHS esters.

1. Preparation of Appel Salt

ClCH$_2$CN + Cl$_2$S$_2$ ⟶ 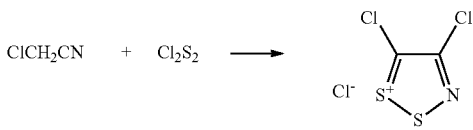

A 500-mL round-bottomed flask was charged with chloroacetonitrile (20 mL), sulfur monochloride (120 mL), and $CH_2Cl_2$ (110 mL) under argon. The reaction stirred under argon for 3 days while a brown precipitate formed. The precipitate was collected by suction filtration and washed with $CH_2Cl_2$ (300 mL) and hexanes (300 mL). The washed solid was vacuum dried to give the product as a brown solid (75% yield).

2. Preparation of 2-Cyanobenzothiazoles

The following procedure is for the preparation of 5,7-dichloro-6-hydroxy-2-cyanobenzothiazole. The preparation of 5,7-difluoro-6-hydroxy-2-cyanobenzothiazole followed the same procedure with very similar results.

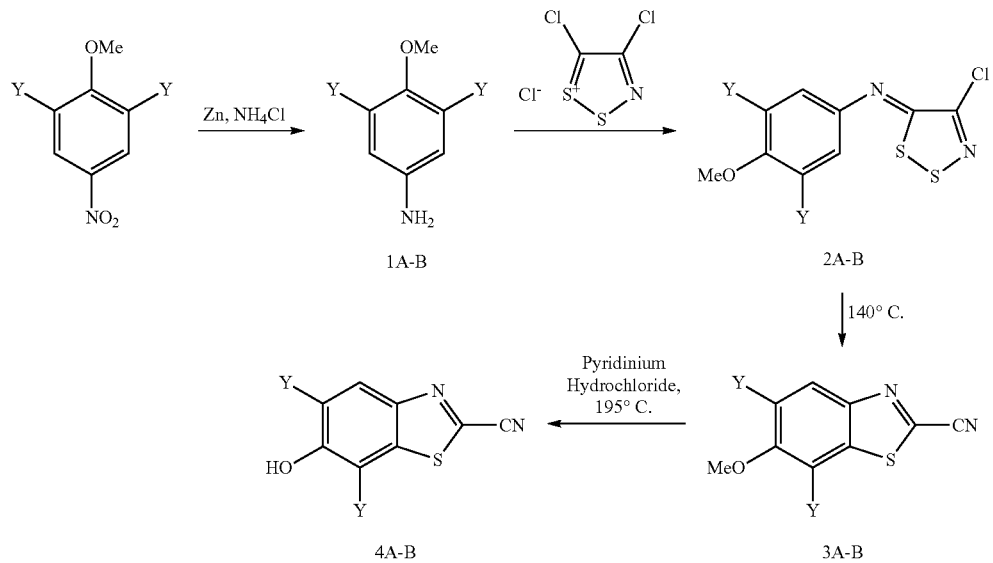

Y = Cl, F

A 5-L round-bottomed flask was charged with 1,3-dichloro-2-methoxynitrobenzene (0.33 moles), ammonium chloride (3.3 moles), and ethanol (1200 mL). Zinc dust (3.3 moles) is added rapidly to the stirred mixture. The reaction mixture warmed to near reflux after several minutes and was then allowed to cool to room temperature. After stirring overnight, the suspension was filtered to remove residual zinc and ammonium chloride. The filtrate was concentrated under reduced pressure and the resulting solid was resuspended in $CH_2Cl_2$ (1500 mL). The suspension was filtered and the filtrate concentrated under reduced pressure to give the substituted aniline as a white solid (0.33 moles).

| 1A | Y = Cl | $^1$H NMR (400 MHz, CDCl$_3$): δ 6.601 (s, 2H), 3.811 (s, 3H), 3.6-3.7 (broad s, 2H) |
| --- | --- | --- |
| 1B | Y = F | $^1$H NMR (400 MHz, CDCl$_3$): δ 6.22 (m, 2H), 3.860 (s, 3H), 3.6-3.7 (broad s, 2H) |

A 2-L three-necked round-bottomed flask was oven-dried and cooled under an argon flow. The flask was charged with 1,3-dichloro-2-methoxyaniline (0.33 moles), pyridine (75 mL), and $CH_2Cl_2$ (550 mL). The appel salt (0.33 moles) was added in portions over 5 minutes causing the solution to reflux. TLC showed the complete disappearance of the aniline after 15 minutes. The reaction mixture was concentrated to an orange solid. The solid was dissolved in 2.5 L of ethyl acetate. The organic solution was washed with type 1 water (2×1000 mL) and brine (1000 mL). The washed organic layer was dried over anhydrous $Na_2SO_4$ and concentrated to give the appel salt adduct as a solid.

| 2A | Y = Cl | $^1$H NMR (400 MHz, CDCl$_3$): δ 7.203 (s, 2H), 3.933 (s, 3H) |
| --- | --- | --- |
| 2B | Y = F | $^1$H NMR (400 MHz, CDCl$_3$): δ 6.87 (m, 2H), 4.030 (s, 3H) |

A 500-mL three-necked round-bottomed flask was equipped with and argon inlet line and a water-cooled condenser with a bubbler connected to the outlet. The flask was charged with appel salt adduct (0.134 moles) and heated to a surface temperature of 140° C. for 1 hour. Toluene (50 mL) was added and the reaction was cooled to 90° C. $CH_2Cl_2$ (100 mL) and silica (50 g) were added. The resulting slurry was filtered and the filter cake was washed with $CH_2Cl_2$ (200 mL). The combined filtrate and washes were concentrated and flash chromatography ($CH_2Cl_2$/hexanes) provided the 5,7-dichloro-6-methoxy-2-cyanobenzothiazole as a solid (0.031 moles).

| 3A | Y = Cl | $^1$H NMR (400 MHz, CDCl$_3$): δ 8.194 (s, 1H), 4.027 (s, 3H) |
| --- | --- | --- |
| 3B | Y = F | $^1$H NMR (400 MHz, CDCl$_3$): δ 7.981 (dd, J = 10 Hz & 1.6 Hz, 1H), 4.156 (s, 3H) |

A 250-mL round-bottomed flask was charged with pyridinium hydrochloride (160 mmoles) and 5,7-dichloro-6-methoxy-2-cyanobenzothiazole (8.2 mmoles). The reaction was padded under argon and then heated at 195° C. for 3 hours. After cooling to room temperature, type 1 water (150 mL) was added and the mixture was sonicated to dissolve the solids. The aqueous solution was extracted with ethyl acetate. The ethyl acetate was dried over anhydrous $Na_2SO_4$ and concentrated to give the product as a yellow solid (2.8 mmoles).

| | | |
|---|---|---|
| 4A | Y = Cl | $^1$H NMR (400 MHz, acetone- $d_6$): δ 8.313 (s) |
| 4B | Y = F | $^1$H NMR (400 MHz, acetone- $d_6$): δ 8.385 (dd, J = 10.4 Hz & 1.6 Hz) |

3. Preparation of Amino Acids

5A-F

| | W | $Z_1$ | LH | $X_2$ |
|---|---|---|---|---|
| 5A | H | H | OH | O |
| 5B | H | Me | OH | S |
| 5C | Me | H | OH | S |
| 5D | Me | H | NHCH2CO2H | S |
| 5E | Me | H | NHCH2CH2CO2H | S |
| 5F | Me | H | NHCH2CH2CH2CH2CH2CO2H | S |

Synthesis of Modified Penicillamines

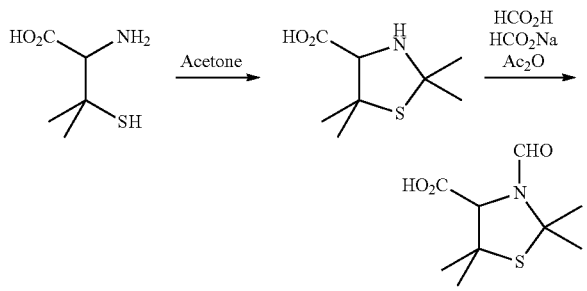

A 2000-mL round-bottomed flask was charged with DL-penicillamine (10 g) and acetone (1000 mL). The reaction was refluxed until all the solid had dissolved (approximately 24 hours). The reaction mixture was filtered while hot and cooled to room temperature overnight. A small amount of crystals had formed overnight. The reaction mixture was kept at −20° C. overnight. The resulting solids were collected by suction filtration and washed with acetone (300 mL). The thiazole product was dried under argon (11.9 g). $^1$H NMR (400 MHz, DMSO-$d_6$): δ 3.750 (s, 1H), 1.556 (s, 6H), 1.438 (s, 3H), 1.185 (s, 3H)

A 250-mL round-bottomed flask was charged with thiazole acid (11.9 g) and sodium formate (4.3 g) under argon. Formic acid (98%, 100 mL) was added and the reaction mixture stirred under argon. The reaction mixture was cooled to 0° C. in an ice/water bath. Acetic anhydride (33.3 mL) was added drop wise over 45 minutes while taking care that the temperature remained below 5° C. The ice/water bath was removed and the reaction was stirred overnight at room temperature. The solvents were removed under vacuum at 35° C. producing a white solid. The solid was stirred in type 1 water (200 mL) and collected by suction filtration. The solid was washed with type 1 water (100 mL) and air-dried (7.4 g). The combined filtrate and wash was extracted with ethyl acetate (3×300 mL). The extracts were combined, dried over $Na_2SO_4$, and filtered. The filtrate was concentrated to give a pale yellow solid (6.8 g). $^1$H NMR showed the two solids to be an isomeric mixture (~85:15) of the target compound. $^1$H NMR (400 MHz, DMSO-$d_6$ 12.916 (S, 1H), 8.446 (s, 0.86H), 8.195 (s, 0.14H), 4.641 (s, 0.15H), 4.502 (s, 0.85H), 1.828 (s, 6H), 1.590 (s, 3H), 1.362 (s, 3H)

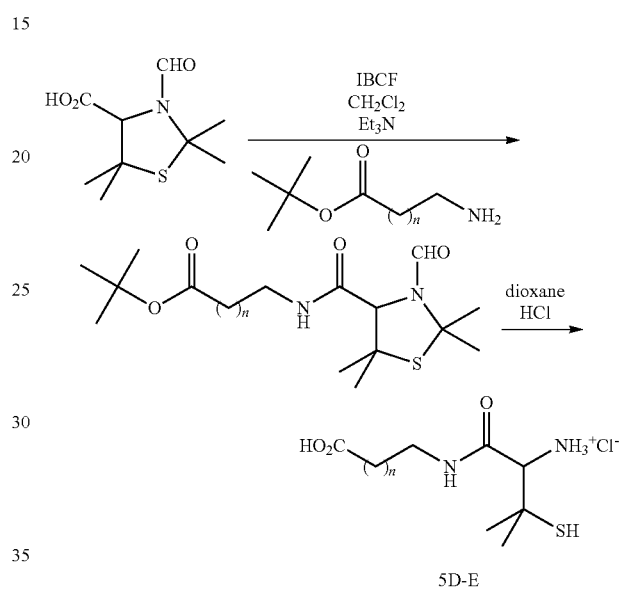

5D-E n = 0, 1

A round-bottomed flask was charged with formylated thiazole acid (1 equivalent), triethylamine (2 equivalents), and $CH_2Cl_2$. The reaction mixture was stirred at 0° C. in an ice/water bath under argon. Isobutylchloroformate (1 equivalent) was added via syringe. After the reaction mixture had stirred for 1 hour, the amino ester (1 equivalent) was added. The ice/water bath was removed and the reaction mixture stirred overnight at room temperature. The reaction mixture was washed with 1.0 M HCl (75 mL), 5% $NaHCO_3$ (75 mL), and type 1 water (75 mL). The organic layer was concentrated under reduced pressure and flash chromatography (50:50 ethyl acetate:hexanes) gave the target product (60-70% yield). $^1$H NMR showed an isomeric mixture of products.

n=0 $^1$H NMR (400 MHz, $CDCl_3$): 8.389 (s, 0.88H), 8.328 (s, 0.12H), 6.932 (m, 0.15H), 6.383 (m, 0.82), 4.620 (s, 0.82H), 4.367 (s, 0.15H), 4.030 (dd, J=18.4 Hz & 5.2 Hz, 1H), 3.91 (m, 1H), 2.00-1.94 (m, 6H), 1.70-1.59 (m, 3H), 1.47 (m, 12H)

n=1 $^1$H NMR (400 MHz, $CDCl_3$): 8.358 (s, 0.79H), 8.291 (s, 0.15H), 6.973 (m, 0.15H), 6.486 (m, 0.78), 4.418 (s, 0.80H), 4.313 (s, 0.13H), 3.6-3.4 (m, 2H), 2.43 (m, 2H), 2.00-1.94 (m, 6H), 1.68-1.60 (m, 3H), 1.44 (m, 12H)

A round-bottomed flask was charged with the formylated thiazole ester, and dioxane:2.0 M HCl (50:50). The reaction mixture was heated at 85° C. under argon overnight. After cooling to room temperature, the reaction mixture was concentrated under reduced pressure to give the modified penicillamine as a gummy solid.

n=0 $^1$H NMR showed an isomeric mixture of products. $^1$H NMR (400 MHz, D$_2$O): 4.128 & 4.083 (s, 1H), 4.043 & 4.000 (s, 2H), 1.557 (s, 3H), 1.481 (s, 3H)

n=1 $^1$H NMR (400 MHz, D$_2$O): 3.702 (s, 1H), 3.45-3.38 (m, 1H), 3.27-3.19 (m, 1H), 2.441 (m, 2H), 1.295 (s, 3H), 1.233 (s, 3H)

Synthesis of Methylated Cysteine

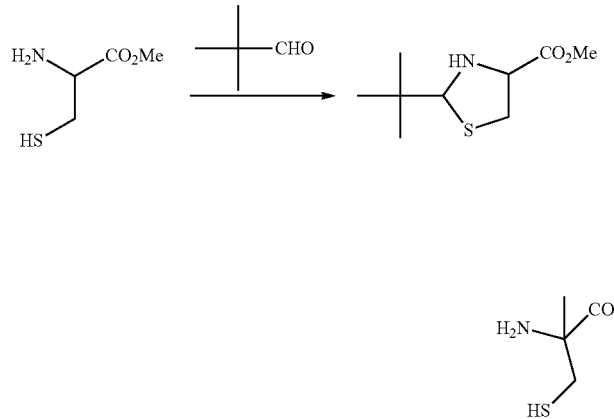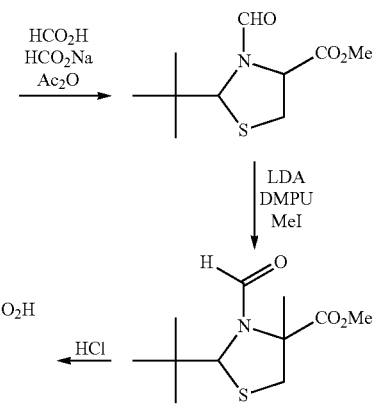

Cysteine methyl ester (8.6 g), pivalaldehyde (11 mL), and triethylamine (8 mL) were stirred in pentane. The reaction mixture was refluxed while water was removed via a Dean-Stark trap. After 36 hours, the reaction was cooled to room temperature and solids formed. The solids were collected by suction filtration and washed with ether.

A 100-mL round-bottomed flask was charged with thiazole ester (4.0 g), formic acid (98%, 30 mL) and sodium formate (1.5 g). The reaction mixture was stirred under argon and cooled to 0° C. in an ice/water bath. Acetic anhydride (5.7 mL) was added drop wise over 30 minutes while taking care that the temperature remained below 5° C. The ice/water bath was removed and the reaction was stirred overnight at room temperature. The solvents were removed under vacuum and the resulting solid was stirred in type 1 water (100 mL). The pH was adjusted to 7-8 by the addition of solid NaHCO$_3$. The aqueous solution was extracted with ether (3×100 mL). The extracts were combined, dried over Na$_2$SO$_4$, and filtered. The filtrate was concentrated to give a solid. The solids were recrystallized from ethyl acetate/hexanes. $^1$H NMR (400 MHz, CDCl$_3$): 8.317 (s, 1H), 4.858 (t, J=8.8 Hz, 1H), 4.708 (s, 1H), 3.739 (s, 3H), 3.258 (m, 2H), 1.000 (s, 9H)

A solution of lithium diisopropylamine (12 mmoles) in anhydrous THF (100 mL) at −78° C. was stirred under argon. 1.3-Dimethyl-3,4,5,6-tetrahydro-2(1H)-pyrimidinone (DMPU, 10 mL) was added and the reaction mixture stirred for 90 minutes. Formylated thiazole ester was added (10 mmoles) and the reaction mixture was stirred at −78° C. for 1 hour. MeI (15 mmoles) was added and the reaction mixture was stirred at −78° C. for 2 hours. The dry ice/acetone bath was removed and the reaction mixture was stirred at room temperature overnight. The reaction mixture was concentrated under reduced pressure and the residue was taken up in brine. The aqueous solution was extracted with ether (100 mL). The extract was dried over Na$_2$SO$_4$, and filtered. The filtrate was concentrated to give a solid. The solid was purified by flash chromatography with 10% ethyl acetate/hexanes. $^1$H NMR showed a diastereomeric mixture of products. $^1$H NMR (400 MHz, CDCl$_3$) major product: 8.252 (s, 1H), 5.263 (s, 1H), 3.738 (s, 3H), 3.293 (d, J=11.6 Hz, 1H), 2.695 (d, J=11.2 Hz, 1H), 1.038 (s, 9H); minor product: 8.377 (s, 0.4H), 5.274 (s, 0.4H), 3.790 (s, 1.3H), 3.612 (d, J=12 Hz, 0.5H), 2.831 (d, J=12 Hz, 1H), 0.929 (s, 4.6H)

The methylated thiazole ester (1.8 g) and 5 M HCl (30 mL) were heated at 105° C. for 3 days. The reaction mixture was cooled to room temperature and extracted with ethyl acetate (2×100 mL). The aqueous phase was concentrated under reduced pressure to give a gummy solid.

4. Preparation of 6-Hydroxy Luciferin Acids

This is a typical procedure for the preparation of the basic luciferin structure.

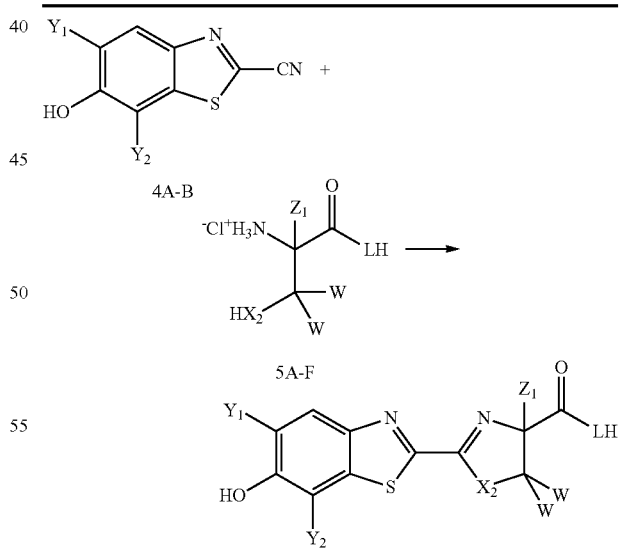

| | W | Z$_1$ | LH | X$_2$ | Y$_1$/Y$_2$ |
|---|---|---|---|---|---|
| 6A | H | H | OH | O | F |
| 6B | H | Me | OH | S | F |
| 6C | Me | H | OH | S | F |
| 6D | Me | H | NHCH$_2$CO$_2$H | S | F |

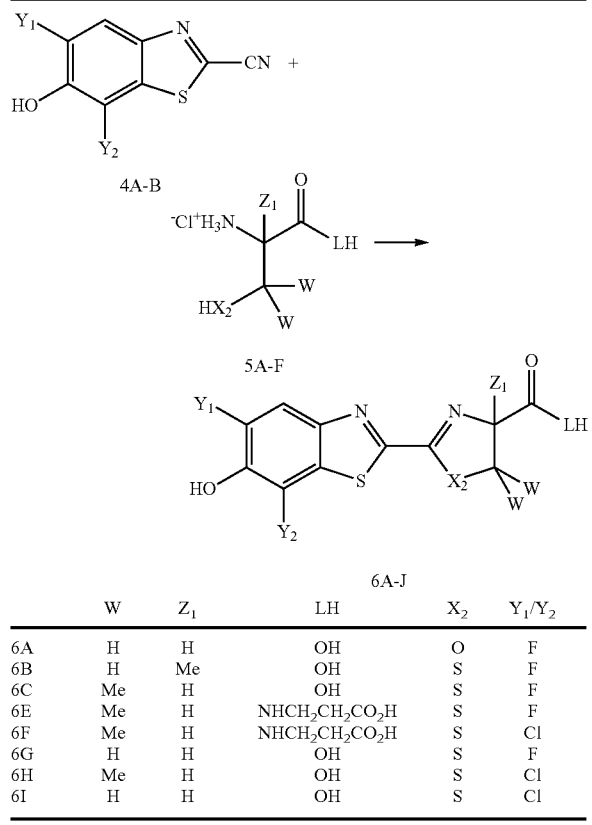

| | W | $Z_1$ | LH | $X_2$ | $Y_1/Y_2$ |
|---|---|---|---|---|---|
| 6A | H | H | OH | O | F |
| 6B | H | Me | OH | S | F |
| 6C | Me | H | OH | S | F |
| 6E | Me | H | NHCH$_2$CH$_2$CO$_2$H | S | F |
| 6F | Me | H | NHCH$_2$CH$_2$CO$_2$H | S | Cl |
| 6G | H | H | OH | S | F |
| 6H | Me | H | OH | S | Cl |
| 6I | H | H | OH | S | Cl |

A 100-mL round-bottomed flask was charged with the cyanobenzothiazole (0.5 mmole) and methanol (25 mL). The stirred reaction mixture was sparged with argon for 1 hour. An argon-sparged solution of the amino acid (1 mmole) in water with a pH of 9 (pH adjustment by the addition of Na$_2$CO$_3$) was prepared and added. The reaction mixture was stirred for 2 hours under argon and TLC indicated the reaction was completed. The reaction was concentrated under reduced pressure to ~10 mL and diluted with type 1 water (40 mL). The aqueous solution was extracted with ethyl acetate (3×75 mL) and the extracts were set aside. The aqueous solution was acidified to pH 2 by the drop wise addition of concentrated HCl. The acidified aqueous solution was extracted again with ethyl acetate (3×75 mL). The six extracts were combined, dried over anhydrous Na$_2$SO$_4$, and concentrated to give the product as a solid (40-90% yields).

6A $^1$H NMR (400 MHz, CD$_3$OD): 7.688 (dd, J=11 Hz & 1.4 Hz, 1H), 5.017 (dd, J=10.2 Hz & 8.2 Hz, 1H), 4.774 (m, 2H)

6B $^1$H NMR (400 MHz, CDCl$_3$): 7.795 (dd, J=10 Hz & 1.6 Hz, 1H), 3.932 (d, J=11.8 Hz, 1H), 3.434 (d, J=11.8 Hz, 1H), 1.688 (s, 3H)

6C $^1$H NMR (400 MHz, CD$_3$OD): 7.646 (dd, J=10.4 Hz & 1.2 Hz, 1H), 4.935 (s, 1H), 1.778 (s, 3H), 1.488 (s, 3H)

6D $^1$H NMR (400 MHz, CD$_3$OD): 8.379 (broad s, 1H), 7.658 (d, J=10 Hz, 1H), 4.758 (s, 1H), 4.000 (d, J=6 Hz, 2H), 1.829 (s, 3H), 1.448 (s, 3H)

6E $^1$H NMR (400 MHz, CD$_3$OD): 8.190 (broad s, 1H), 7.647 (d, J=10.4 Hz, 1H), 4.705 (s, 1H), 3.56-3.50 (m, 2H), 2.558 (t, J=6.6 Hz, 2H), 1.814 (s, 3H), 1.395 (s, 3H)

6F $^1$H NMR (400 MHz, CD$_3$OD): 8.271 (broad s, 1H), 8.093 (s, 1H), 4.794 (s, 1H), 3.610 (m, 2H), 2.640 (t, J=6.6 Hz, 2H), 1.898 (s, 3H), 1.478 (s, 3H)

6G $^1$H NMR (400 MHz, acetone-d$_6$): 9.838 (s, 1H), 7.810 (dd, J=10.8 Hz, & 1.6 Hz, 1H), 5.504 (t, J=9.2 Hz, 1H), 3.860 (m, 2H)

6H $^1$H NMR (400 MHz, DMSO-d$_6$): 8.266 (s, 1H), 5.007 (s, 1H), 1.725 (s, 1H), 1.447 (s, 1H)

6I $^1$H NMR (400 MHz, acetone-d$_6$): 8.149 (s, 1H), 5.505 (t, J=9.2 Hz, 1H), 3.855 (m, 2H)

Compound 6J (L=NH$_2$(CH$_2$)$_5$COOH) was prepared in three steps starting from compound 6H. Reaction of carboxylic acid 6H with N-hydroxysuccinimide and DCC produced NHS ester 7H which was coupled with methyl 6-aminohexanoate. The resulting methyl ester was hydrolyzed with base to produce 6J.

5. Preparation of Luciferin NHS Esters

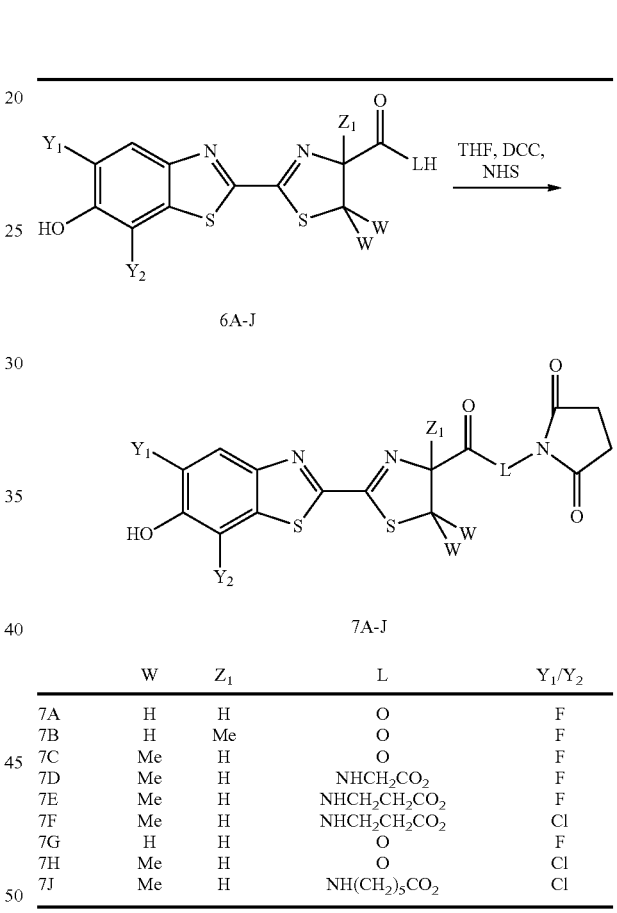

| | W | $Z_1$ | L | $Y_1/Y_2$ |
|---|---|---|---|---|
| 7A | H | H | O | F |
| 7B | H | Me | O | F |
| 7C | Me | H | O | F |
| 7D | Me | H | NHCH$_2$CO$_2$ | F |
| 7E | Me | H | NHCH$_2$CH$_2$CO$_2$ | F |
| 7F | Me | H | NHCH$_2$CH$_2$CO$_2$ | Cl |
| 7G | H | H | O | F |
| 7H | Me | H | O | Cl |
| 7J | Me | H | NH(CH$_2$)$_5$CO$_2$ | Cl |

This is a typical procedure for the preparation of the luciferin NHS esters.

A 10-mL round-bottomed flask was padded with argon and charged with the luciferin (0.3 mmole), N-hydroxysuccinimide (0.3 mmole), and DCC (0.305 mmole). Anhydrous THF (4 mL) was added and the reaction mixture was stirred for 3 hours. The solvent was removed under reduced pressure and a small volume of CH$_2$Cl$_2$ was added. A white precipitate formed and was removed by filtration. The filtrate was concentrated under reduced pressure to form a gummy solid. The solid was dissolved in a minimum of THF and the addition of hexanes resulted in the solid reforming. The solvents were decanted and the procedure was repeated 2 additional times to give the product as a yellow solid (60% yields).

7B $^1$H NMR (400 MHz, CDCl$_3$): 7.650 (m, 1H), 4.093 (d, J=11.4 Hz, 1H), 3.481 (d, J=11.4 Hz, 1H), 1.814 (s, 3H)

7C ¹H NMR (400 MHz, CDCl₃): 7.660 (dd, J=10.2 Hz & 1.4 Hz, 1H), 5.153 (s, 1H), 2.858 (s, 4H), 1.874 (s, 3H), 1.653 (s, 3H)

7D ¹H NMR (400 MHz, CDCl₃): 7.678 (d, J=10 Hz, 1H), 7.608 (broad s, 1H), 4.713 (s, 1H), 4.614 (dd, J=18 Hz & 6.6 Hz, 1H), 4.389 (dd, J=18 Hz & 5.4 Hz, 1H0, 2.829 (s, 4H), 1.907 (s, 3H), 1.447 (s, 3H)

7E ¹H NMR (400 MHz, CDCl₃): 7.670 (d, J=10 Hz, 1H), 7.616 (broad s, 1H), 4.660 (s, 1H), 3.82-3.65 (m, 2H), 2.899 (t, J=6 Hz, 2H), 2.789 (s, 4H), 1.899 (s, 3H), 1.412 (s, H)

7F ¹H NMR (400 MHz, CDCl₃): 8.073 (s, 1H), 7.653 (broad s, 1H), 4.699 (s, 1H), 3.9-3.7 (m, 2H), 2.932 (t, J=6.0 Hz, 2H), 2.820 (s, 4H), 1.940 (s, 3H), 1.451 (s, 3H)

7G ¹H NMR (400 MHz, acetone-d₆): 7.840 (dd, J=10.0 Hz & 1.6 Hz, 1H), 5.962 (dd, J=10.2 Hz & 8.2 Hz, 1H), 4.127 (t, J=10.8 Hz, 1H), 3.914 (dd, J=11.6 Hz & 8 Hz, 1H), 2.935 (s, 4H)

7H ¹H NMR (400 MHz, acetone-d₆): 8.13 (s, 1H), 5.59 (s, 1H), 2.33 (s, 4H), 1.89 (s, 3H), 1.64 (s, 3H)

7J ¹H NMR (400 MHz, acetone-d₆): 9.53 (broad s, 1H), 8.10 (s, 1H), 7.78 (m, 1H), 4.69 (s, 1H), 3.22-3.42 (m, 2H), 2.81 (s, 4H), 2.62 (t, 2H), 1.86 (s, 3H), 1.76-1.69 (m, 2H), 1.63-1.56 (m, 2H), 1.50-1.44 (m, 2H), 1.42 (s, 3H)

6. Preparation of Luciferin Maleimide Derivatives

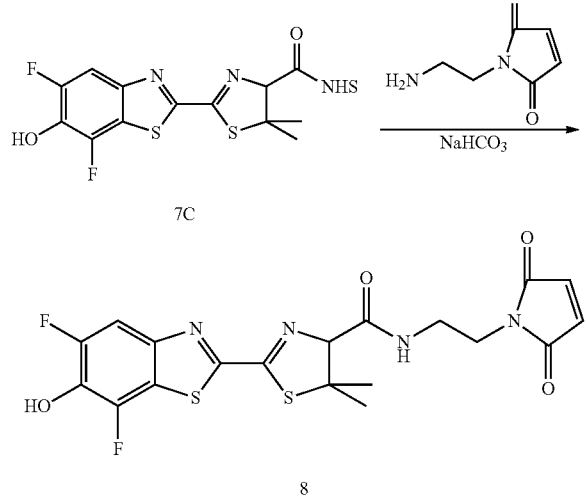

The luciferin NHS ester (22 mg) was stirred in anhydrous THF. N-(2-aminoethyl)maleimide-trifluoroacetic acid (13 mg) was added followed by aqueous NaHCO₃. The mixture was stirred for 4 hours and then concentrated under reduced pressure. The mixture was dissolved in 5 mL of water and extracted with ethyl acetate. The extract was dried over anhydrous Na₂SO₄ and concentrated under reduced pressure. The solids were dissolved in acetone and hexanes was added to generate a precipitate that was air-dried (13 mg). ¹H NMR (400 MHz, DMSO-d₆): 8.118 (m, 1H), 7.886 (d, J=10.8 Hz, 1H), 6.972 (s, 2H), 4.670 (s, 1H), 3.38 (m, 2H), 3.33 (m, 2H), 1.678 (s, 3H), 1.264 (s, 3H)

Preparation of Fluorescent Dye1 (7H):

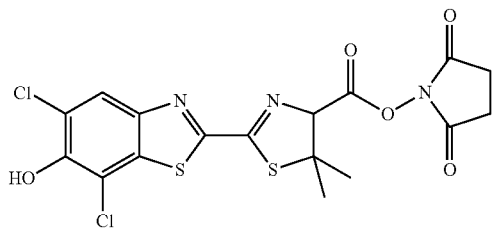 [SMILES: CC1(C)SC(c2nc3cc(Cl)c(O)c(Cl)c3s2)=NC1C(=O)ON1C(=O)CCC1=O]

Fluorescent dye 1 (LD1; 7H) was synthesized using the synthesis scheme described above. Briefly, 2-cyano-5,7-dichloro-6-hydroxybenzothiazole (4A), synthesized using the method describe above was reacted with D,L-Penicillamine (5C) under conditions described in detail above to afford 5,7-dichloro-6-hydroxy luciferin acid (6H).

For the synthesis of 5,7-dichloro-6-hydroxy luciferin NHS ester, the dichloro-6-hydroxy luciferin acid (6H) was reacted with N-hydroxysuccinimide in the presence of DCC as described above. The resulting NHS ester (7H) was purified and characterized by NMR as described above.

Preparation of Fluorescent Dye2 (7J):

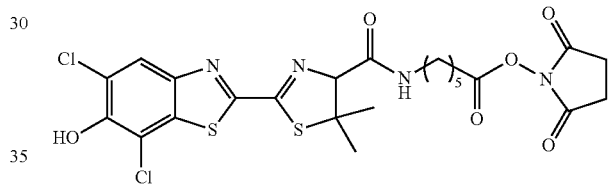

Fluorescent dye 2 (LD2; Compound 7J) was synthesized using synthesis scheme described above, except that 2-cyano-5,7-dichloro-6-hydroxybenzothiazole (4A), was reacted with compound 5F under conditions described in detail above to afford 5,7-dichloro-6-hydroxy luciferin acid (6J).

The dichloro-6-hydroxy luciferin acid (6J) was next reacted with N-hydroxysuccinimide in the presence of DCC as described above to yield the NHS ester (7J), which was purified and analyzed by NMR as described above.

Preparation of Fluorescent Dye3 (7C):

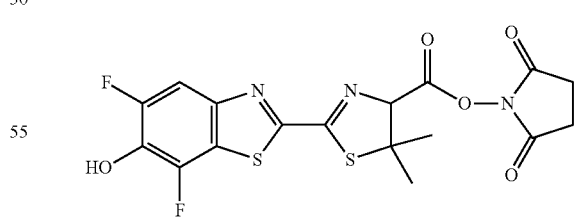

Fluorescent dye 3 (LD3; 7C) was synthesized using synthesis scheme as described above, except that 2-cyano-5,7-difluoro-6-hydroxybenzothiazole (4B), was reacted with D,L-Penicillamine (5C) under conditions described in detail above to afford 5,7-difloro-6-hydroxy luciferin acid (6C).

The difloro-6-hydroxy luciferin acid (6C) was next reacted with N-hydroxysuccinimide in the presence of DCC as described above to yield the 5,7-difloro-6-hydroxy luciferin NHS ester (7C), which was purified and analyzed by NMR as described above.

Preparation of Fluorescent Dye4 (7B):

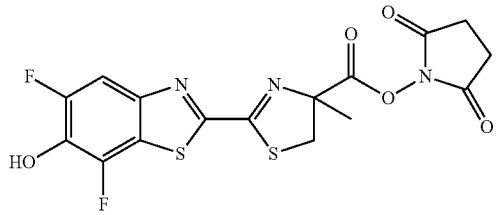 [SMILES: CC1(C(=O)ON2C(=O)CCC2=O)CSC(c2nc3cc(F)c(O)c(F)c3s2)=N1]

Fluorescent dye 4 (LD4; 7B) was synthesized using synthesis scheme as described above, except that 2-cyano-5,7-difloro-6-hydroxybenzothiazole (4B), was reacted with compound 5B under conditions described in detail above to afford 5,7-difloro-6-hydroxy luciferin acid (6C). The 5,7-difloro-6-hydroxy luciferin acid (6C) was next reacted with N-hydroxysuccinimide in the presence of DCC as described above to yield the 5,7-difloro-6-hydroxy luciferin NHS ester (7C), which was purified and analyzed by NMR as described above.

difluoro-6-hydroxybenzothiazole (4B), was reacted with compound 5E under conditions described in detail above to afford 5,7-difloro-6-hydroxy luciferin acid (6E). The 5,7-difloro-6-hydroxy luciferin acid (6E) was next reacted with N-hydroxysuccinimide in the presence of DCC as described above to yield the 5,7-difloro-6-hydroxy luciferin NHS ester (7E), which was purified and analyzed by NMR as described above.

Preparation of Fluorescent Dye6 (9B)

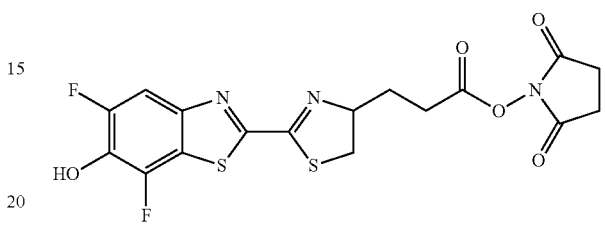

Fluorescent dye 6 (LD6) was synthesized using the scheme described below.

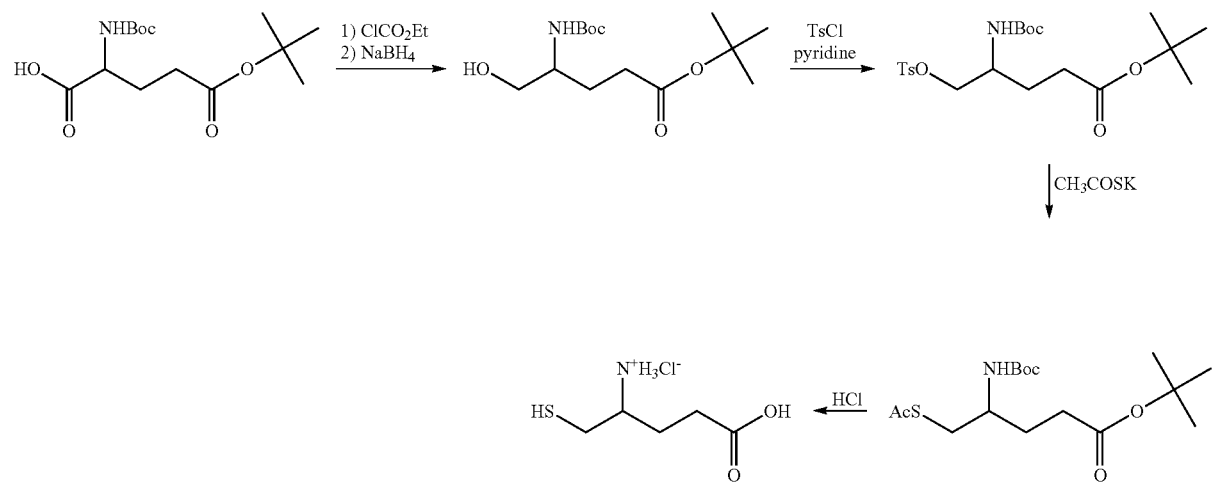

Preparation of Fluorescent Dye5 (7E)

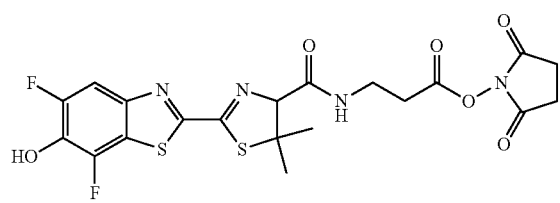 [SMILES: CC1(C)SC(c2nc3cc(F)c(O)c(F)c3s2)=NC1C(=O)NCCC(=O)ON1C(=O)CCC1=O]

Fluorescent dye 5 (LD5; 7E) was synthesized using synthesis scheme as described above, except that 2-cyano-5,7-

N-Boc-L-glutamic acid γ-t-butyl ester (4.3 g) was stirred in $CH_2Cl_2$ at 0° C. Triethylamine (2 mL) was added via syringe followed by the addition of ethyl chloroformate (1.4 mL). The reaction mixture was stirred for 60 minutes, filtered, and the solids were washed with anhydrous THF. The filtrate and washes were combined and transferred to an addition funnel. The solution was added drop wise over 30 minutes to a stirred solution of $NaBH_4$ in $H_2O$ (20 mL) at 0° C. The reaction mixture was stirred at 0° C. for 5 hours before stirring at room temperature overnight. The reaction mixture was concentrated under reduced pressure and the residue was diluted with ethyl acetate. The solution was washed with water and brine, dried over anhydrous $Na_2SO_4$, and concentrated under reduced pressure. Flash chromatography (20:80 ethyl acetate:hexanes) gave the product as an oil. $^1H$ NMR (400

MHz, CDCl$_3$): 4.814 (broad s, 1H), 3.62-3.49 (m, 3H), 2.496 (broad s, 1H), 2.290 (q, J=6.8 Hz, 2H), 1.83-1.69 (m, 2H), 1.406 (s, 18H)

The amino alcohol (3.5 g) was stirred in pyridine (25 mL) at 0° C. under an argon pad. Tosyl chloride (3.0 g) was added and the reaction mixture stirred at 0° C. for 6 hours. The solution was warmed to room temperature and stirred overnight. The reaction mixture was concentrated under reduced pressure and the resulting solids were dissolved in ethyl acetate. The solution was washed with saturated NaHCO$_3$ followed by brine. The washed solution was dried over anhydrous Na$_2$SO$_4$ and concentrated under reduced pressure. Flash chromatography gave the product as an oil. $^1$H NMR (400 MHz, CDCl$_3$): 7.744 (d, J=8.8 Hz, 2H), 7.311 (d, J=8.8 Hz, 2H), 4.623 (d, J=8.4 Hz, 1H), 4.00-3.91 (m, 2H), 3.739 (broad s, 1H), 2.411 (s, 3H), 2.224 (m, 2H), 1.719 (m, 2H), 1.390 (s, 9H), 1.350 (s, 9H)

A solution of the tosylated ester (3.9 g) and potassium thioacetate (2.9 g) in anhydrous DMF was stirred at room temperature for 3 days. The reaction mixture was diluted with ethyl acetate (300 mL) and washed with brine (3×100 mL). The washed solution was dried over anhydrous Na$_2$SO$_4$ and concentrated under reduced pressure. Flash chromatography (15:85 ethyl acetate:hexanes) gave the product as an oil. $^1$H NMR (400 MHz, CDCl$_3$): 4.522 (d, J=8 Hz, 1H), 3.704 (broad s, 1H), 3.07-2.94 (m, 2H), 2.311 (s, 3H), 2.264 (t, J=7.2 Hz, 2H), 1.80-1.60 (m, 2H), 1.404 (s, 9H), 1.386 (s, 9H)

The thioacetate (2.5 g) was heated in degassed 6 N HCl at 105° C. overnight. The reaction mixture was cooled to room temperature and concentrated under reduced pressure to give a red oil. $^1$H NMR (400 MHz, D$_2$O):

A flask was charged with 2-cyano-5,7-difloro-6-hydroxy-benzothiazole (110 mg) and methanol (25 mL). The stirred reaction mixture was sparged with argon for 1 hour. An argon-sparged solution of the amino acid (300 mg) in water with a pH of 9 (pH adjustment by the addition of Na$_2$CO$_3$) was prepared and added to the reaction mixture in 3 portions at 1 hour intervals. The reaction mixture was stirred overnight. The reaction was concentrated under reduced pressure to ~10 mL and diluted with type 1 water (40 mL). The aqueous solution was extracted with ethyl acetate (50 mL) and the extract was set aside. The aqueous solution was acidified to pH 2 by the drop wise addition of concentrated HCl. The acidified aqueous solution was extracted again with ethyl acetate (2×50 mL). The 2 extracts were combined, dried over anhydrous Na$_2$SO$_4$, and concentrated to give the product as a solid (130 mg). $^1$H NMR (400 MHz, CD$_3$OD): 7.641 (d, J=10.4 Hz, 1H), 4.694 (m, 1H), 3.612 (t, J=8.8 Hz, 1H), 3.179 (t, J=9.4 Hz, 1H), 2.550 (m, 2H), 2.037 (m, 2H)

A flask was padded with argon and charged with the deoxoluciferin acid (41 mg), N-hydroxysuccinimide (15 mg), and DCC (26 mg). Anhydrous THF (4 mL) was added and the reaction mixture was stirred for 3 hours. The reaction solution was filtered to remove solids. Hexanes were added to precipitate solids which were collected by suction filtration. The solid was redissolved in THF and hexanes were added to precipitate solids. The solids were collected by suction filtration and air-dried. $^1$H NMR (400 MHz, CDCl$_3$): 7.666 (dd, J=10.4 Hz & 1.6 Hz, 1H), 4.772 (m, 1H), 3.612 (m, 1H), 3.158 (dd, J=11 Hz & 8.6 Hz, 1H), 3.00-2.86 (m, 2H), 2.821 (s, 4H), 2.188 (m, 2H)

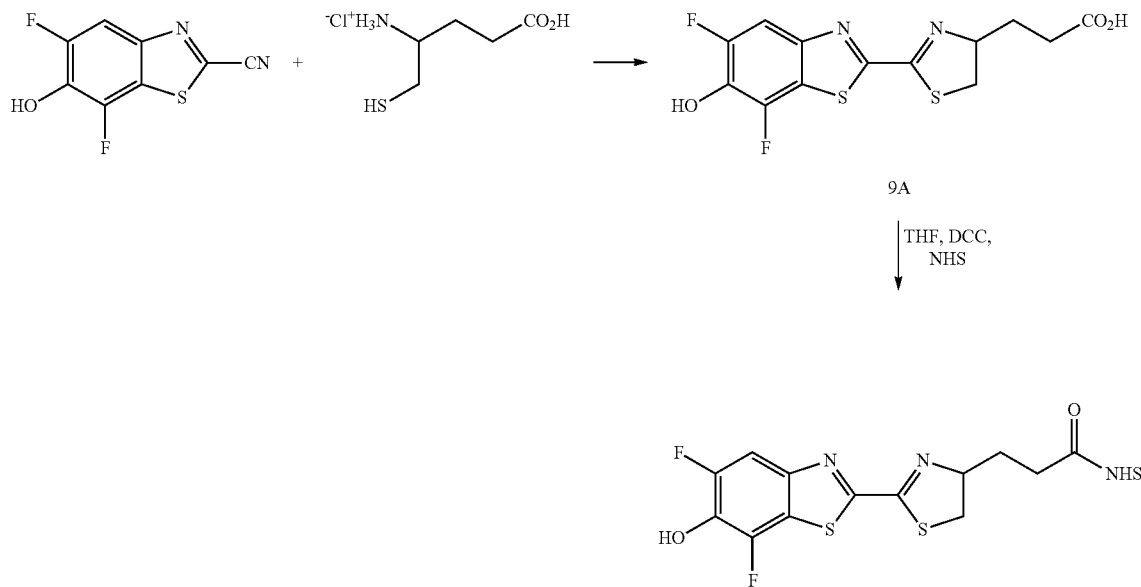

Preparation of Dehydroluciferin (10).

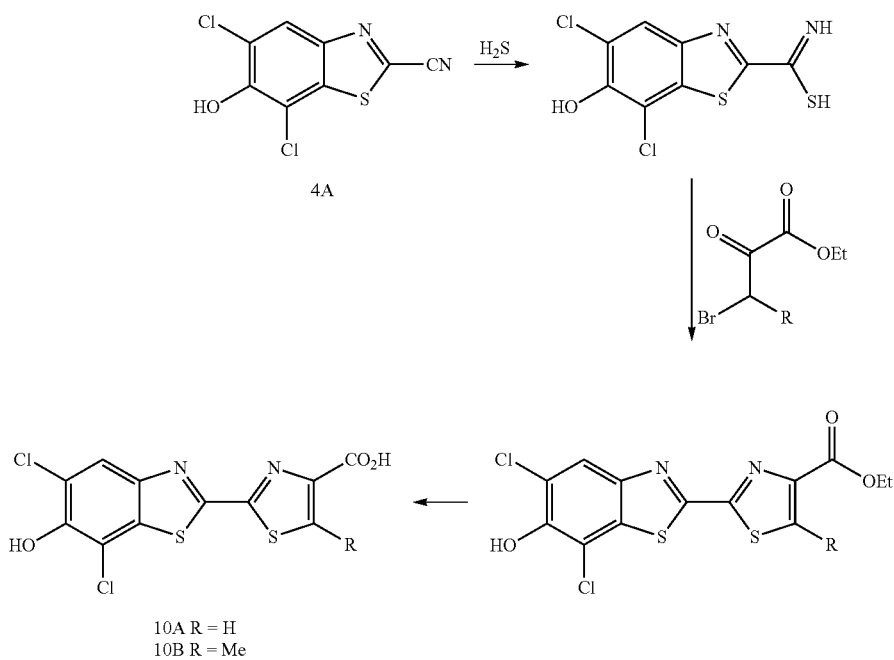

10A R = H
10B R = Me

The following reaction description is for the example 10A and similar reaction conditions were used in the case of 10B. $^1$H NMR data are given for both cases.

2-cyano-5,7-dichloro-6-hydroxybenzothiazole (2.8 mmole) was stirred in pyridine (20 mL) and triethylamine (0.3 mL). Hydrogen sulfide was bubbled through the solution for 4.5 hours. The addition of hydrogen sulfide was stopped and the reaction mixture stirred at room temperature overnight. The reaction mixture was stripped under reduced pressure and the resulting solid was recrystallized from methanol. $^1$H NMR (400 MHz, CD$_3$OD): 8.000 (s, 1H)

The benzothiazole product (55 mg) from above was suspended in methanol (5 mL). Ethyl bromopyruvate (100 mg) was added and the reaction mixture was stirred at room temperature overnight. The reaction mixture was heated at 80° C. for 7 hours. The reaction mixture was cooled to room temperature and solids formed. The solids were collected by suction filtration, washed with methanol, and air-dried (35 mg).

R=H $^1$H NMR (400 MHz, CDCl$_3$): 8.295 (s, 1H), 7.992 (s, 1H), 4.436 (q, J=7 Hz, 2H), 1.414 (t, J=7 Hz, 3H)

R=Me Methyl ester $^1$H NMR (400 MHz, CDCl$_3$): 7.964 (s, 1H), 3.951 (s, 3H), 2.837 (s, 3H)

The dehydroluciferin ethyl ester (30 mg) was suspended in methanol and 1 N NaOH. The reaction was stirred at room temperature for 2 days. The reaction mixture was acidified to pH of 2 with 1 N HCl and extracted with ethyl acetate (2×50 mL). The combined extracts were dried over anhydrous Na$_2$SO$_4$ and concentrated under reduced pressure to give the product as a solid.

10A $^1$H NMR (400 MHz, CD$_3$OD): 8.518 (s, 1H), 8.001 (s, 1H)

10B $^1$H NMR (400 MHz, CD$_3$OD): 7.965 (s, 1H), 2.810 (s, 3H)

8. Preparation of 5-Chloro-4-Hydroxy Luciferin Acid (11A) and NHS Ester (11B)

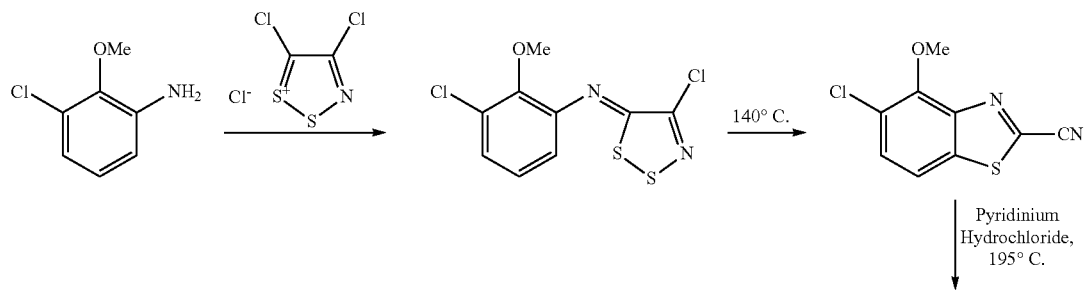

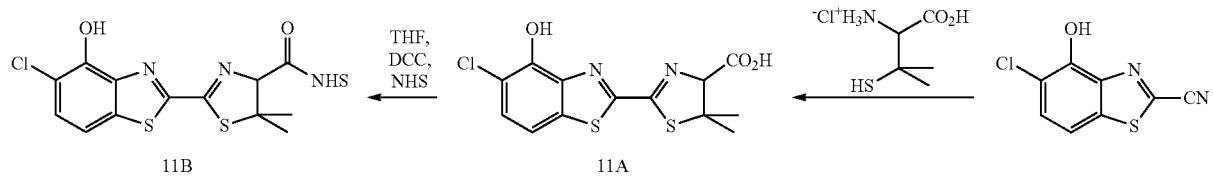

The synthetic route to the 4-hydroxy luciferin acids and NHS esters is identical to the route used to prepare the 6-hydroxy luciferin acids and NHS esters. NMR data is given for the above compounds.

3-Chloro-2-methoxy aniline appel salt: $^1$H NMR (400 MHz, CDCl$_3$): 7.224 (m, 1H), 7.068 (t, J=8.2 Hz, 1H), 6.988 (d, J=8 Hz, 1H), 3.809 (s, 3H)

2-Cyano-5-chloro-4-methoxy benzothiazole: $^1$H NMR (400 MHz, CDCl$_3$): 7.591 (d, J=8.4 Hz, 1H), 7.521 (d, J=8.8 Hz, 1H), 4.349 (s, 3H)

2-Cyano-5-chloro-4-hydroxy benzothiazole: $^1$H NMR (400 MHz, CDCl$_3$): 7.576 (d, J=8.4 Hz, 1H), 7.416 (d, J=8.4 Hz, 1H), 6.702 (s, 1H)

5-Chloro-4-hydroxy dimethyl luciferin acid (11A): $^1$H NMR (400 MHz, CDCl$_3$): 7.451 (d, J=8.4 Hz, 1H), 7.370 (d, J=9.2 Hz, 1H), 6.689 (s, 1H), 4.903 (s, 1H), 1.886 (s, 3H), 1.528 (s, 3H)

5-Chloro-4-hydroxy dimethyl luciferin NHS ester (11B): $^1$H NMR (400 MHz, CDCl$_3$): 7.425 (d, J=8.8 Hz, 1H), 7.354 (d, J=8.4 Hz, 1H), 6.707 (s, 1H), 5.157 (s, 1H), 2.855 (s, 4H), 1.882 (s, 3H), 1.659 (s, 3H)

9. Preparation of 6-Chloro-5-Hydroxy Luciferin Acid (12D)

The synthetic route to the 5-hydroxy luciferin acid is identical to the route used to prepare the 6-hydroxy luciferin acids. NMR data is given for the above compounds.

4-Chloro-3-methoxy aniline appel salt (12A): $^1$H NMR (400 MHz, CDCl$_3$): 7.396 (d, J=8.8 Hz, 1H), 6.78-6.76 (m, 2H), 3.882 (s, 3H)

2-Cyano-6-chloro-5-methoxy benzothiazole (12B): $^1$H NMR (400 MHz, CDCl$_3$): 7.929 (s, 1H), 7.636 (s, 1H), 3.988 (s, 3H)

2-Cyano-6-chloro-5-hydroxy benzothiazole (12C): $^1$H NMR (400 MHz, CDCl$_3$): 7.927 (s, 1H), 7.792 (s, 1H), 5.852 (s, 1H)

6-Chloro-5-hydroxy dimethyl luciferin acid (12D): $^1$H NMR (400 MHz, CD$_3$OD): 7.980 (s, 1H), 7.511 (s, 1H), 4.927 (s, 1H), 1.778 (s, 3H), 1.489 (s, 3H)

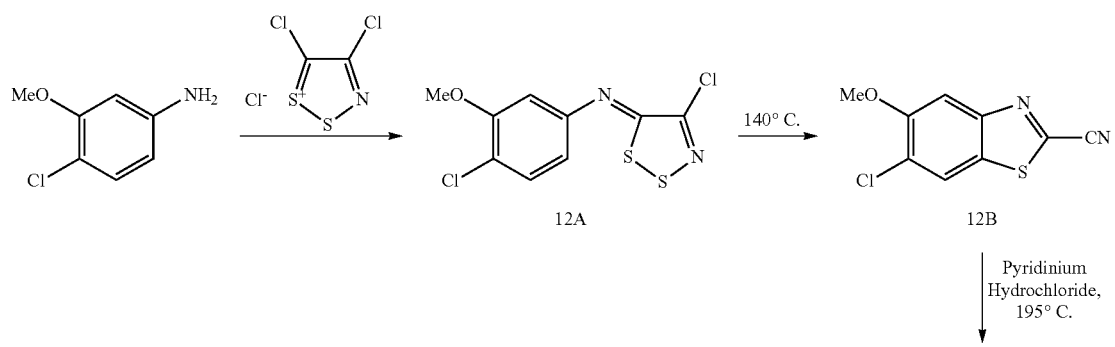

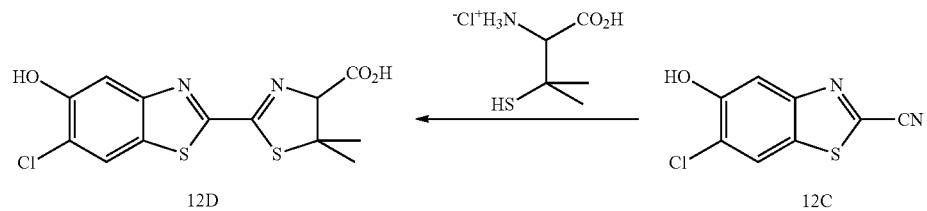

10. Preparation of 5,7-Dimethyl-6-Hydroxy Dimethyl Luciferin Acid (13E)

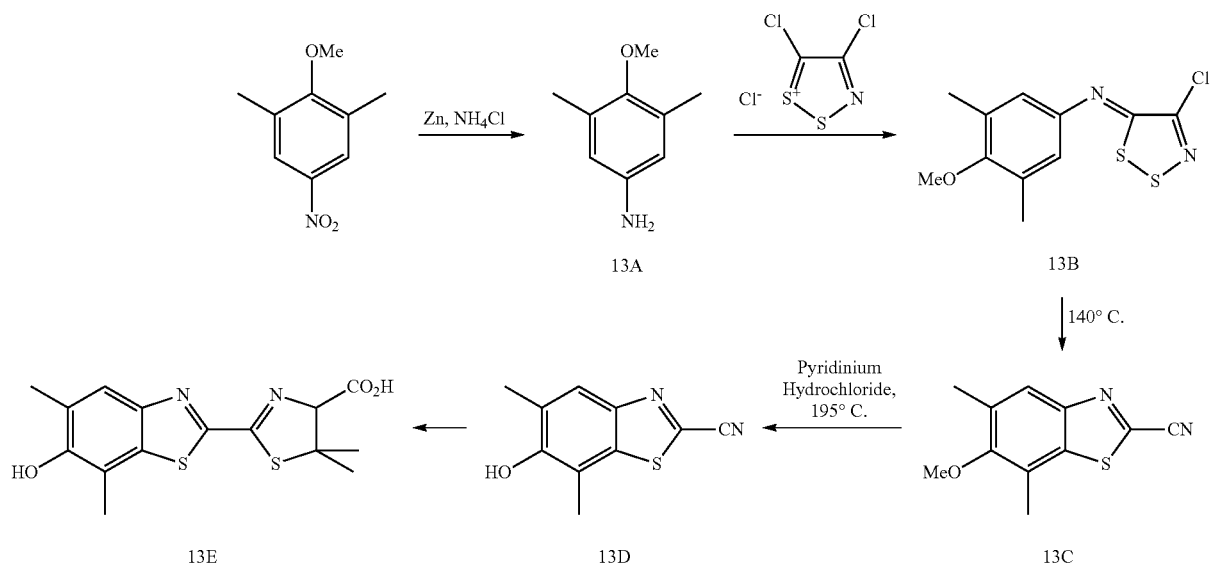

The synthetic route to the 5,7-dimethyl-6-hydroxy dimethyl luciferin acid is identical to the route used to prepare the 6-hydroxy luciferin acids. NMR data is given for the above compounds.

3,5-Dimethyl-4-methoxy aniline (13A): $^1$H NMR (400 MHz, CDCl$_3$): 6.320 (s, 2H), 3.615 (s, 3H), 2.167 (s, 6H)

3,5-Dimethyl-4-methoxy aniline appel salt (13B): $^1$H NMR (400 MHz, CDCl$_3$): 6.905 (s, 2H), 3.711 (s, 3H), 2.278 (s, 6H)

2-Cyano-5,7-dimethyl-6-methoxy benzothiazole (13C): $^1$H NMR (400 MHz, CDCl$_3$): 7.845 (s, 1H), 3.782 (s, 3H), 2.488 (s, 3H), 2.429 (s, 3H)

2-Cyano-5,7-dimethyl-6-hydroxy benzothiazole (13D): $^1$H NMR (400 MHz, CDCl$_3$): 7.805 (s, 1H), 5.2 (broad s, 1H), 2.443 (s, 3H), 2.401 (s, 3H)

5,7-Dimethyl-6-hydroxy dimethyl luciferin acid (13E): $^1$H NMR (400 MHz, CD$_3$OD): 7.641 (s, 1H), 4.905 (s, 1H), 2.401 (s, 3H), 2.333 (s, 3H), 1.777 (s, 3H), 1.491 (s, 3H)

11. Preparation of Trifluoromethyl-substituted Luciferin Acids (14E) and NHS Esters (Fluorescence Dye7; 14F)

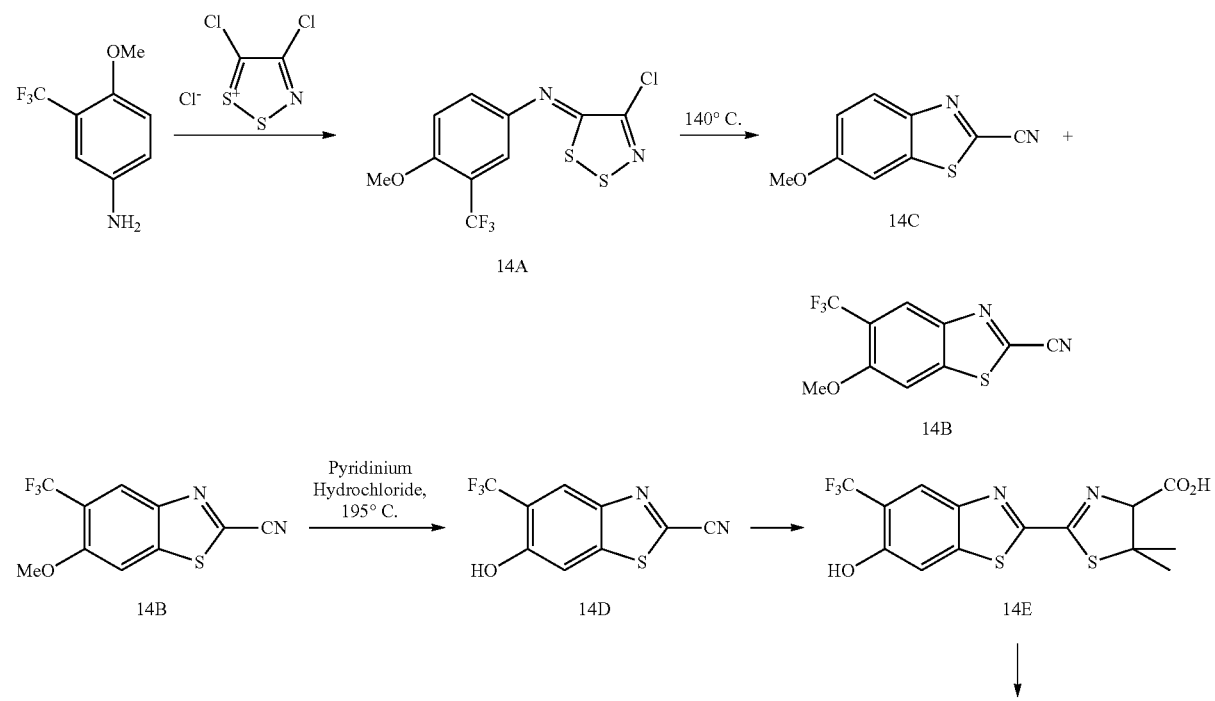

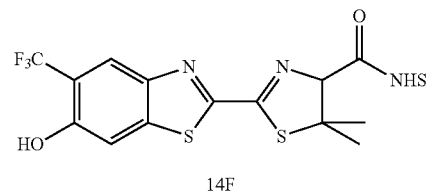

14F

The synthetic route to the trifluoromethyl-substituted luciferin acids and NHS esters is identical to the route used to prepare the 6-hydroxy luciferin acids and NHS esters. NMR data is given for the above compounds.

4-methoxy-3-trifluoromethyl aniline appel salt (14A): $^1$H NMR (400 MHz, CDCl$_3$): 7.522 (d, J=2.4 Hz, 1H), 7.424 (dd, J=8.6 Hz & 2.6 Hz, 1H), 7.064 (d, J=9.2 Hz, 1H), 3.916 (s, 3H)

2-Cyano-5-trifluoromethyl-6-methoxy benzothiazole (14B): $^1$H NMR (400 MHz, CDCl$_3$): 8.384 (s, 1H), 7.451 (s, 1H), 4.033 (s, 3H)

2-Cyano-7-trifluoromethyl-6-methoxy benzothiazole (14C): $^1$H NMR (400 MHz, CDCl$_3$): 8.313 (d, J=8.8 Hz, 1H), 7.374 (d, J=9.2 Hz, 1H), 3.997 (s, 3H)

2-Cyano-5-trifluoromethyl-6-hydroxy benzothiazole (14D): $^1$H NMR (400 MHz, CDCl$_3$): 8.368 (s, 1H), 7.492 (s, 1H)

5-Trifluoromethyl-6-hydroxy dimethyl luciferin acid (14E): $^1$H NMR (400 MHz, CD$_3$OD): 8.168 (s, 1H), 7.479 (s, 1H), 4.927 (s, 1H), 1.779 (s, 3H), 1.492 (s, 3H)

5-Trifluoromethyl-6-hydroxy dimethyl luciferin NHS ester (14F): $^1$H NMR (400 MHz, CDCl$_3$): 8.278 (s, 1H), 7.445 (s, 1H), 5.148 (s, 1H), 2.861 (s, 4H), 1.874 (s, 3H), 1.653 (s, 3H)

Fluorescence Measurement of Luciferin Compounds

The fluorescence measurement experiments were conducted on a HORIBA Jobin Yvon Fluoromax®-3 spectrometer. Typically, the excitation wavelength was set at 405 nm unless otherwise noted. The excitation and emission slits were at 1 nm. A solution of the dye at 20 µM in 25 mM Tris pH 8.0 buffer was used to obtain the fluorescence spectra and determine the intensity at the wavelength of maximum emission shown in Table 6.

TABLE 6

| Luciferin compounds | Fluorescence Intensity at Fluorescence Maxima |
|---|---|
| Compound 6H | 530 nm = 1.1e6 (ex = 405 nm) |
| Compound 6J | 542 nm = 1.75e6 (ex = 405 nm) |
| Compound 6C | 530 nm = 1.1e6 (ex = 405 nm) |
| Compound 6B | 527 nm = 935490 (ex = 405 nm) |
| Compound 6E | 541 nm = 1.3e6 (ex = 405 nm) |
|  | 541 nm = 1.5e6 (ex = 396 nm) |
| Compound 9A | 532 nm = 964121 (ex = 405 nm) |
|  | 532 nm = 1.2e6 (ex = 396 nm) |
| Compound 14E | 532 nm = 570975 (ex = 405 nm) |
|  | 532 nm = 774112 (ex = 396 nm) |
| Compound 10A | 546 nm = 1.6e6 (ex = 405 nm) |

Example 2

The following example provides the description of a method for conjugating the fluorescent dyes of the invention to an antibody molecule.

In a typical experiment, antibody conjugates of Luciferin derivatives are prepared as follows. The antibody of interest is prepared in 50 mM Borate pH 9.0 buffer at 4 mg/ml. The dye reagent is dissolved in anhydrous DMSO to give a concentration of 5 mg/ml. Predetermined amounts of the dye in DMSO are slowly added to the antibody solution with mixing. The reaction is incubated at room temperature for 60 minutes. Thereafter the reaction is quenched with addition glycyl glycine (200 molar excess to the dye used) solution at 75 mg/ml in PBS, 2 mM EDTA. The dye-antibody conjugate is separated desalting on a Sephadex G-50 column equilibrated in PBS. The elution is monitored for 280 nm absorbance and the antibody containing band is collected from the column. The degree of substitution (F/P Value) is determined by measuring absorbance values for the dye-conjugate at 280 nm and at the absorption maxima of the dye peak. The degree of substitution is calculated using the extinction coefficient for the dye being used for the conjugation as shown in Table 7.

TABLE 7

| Dyes of the invention | Extinction Coefficient M$^{-1}$cm$^{-1}$ at Dye absorption maxima |
|---|---|
| 5,7-Dichloroluciferin NHS ester (Dye1) | 14662 |
| 5,7 dichloro luciferin-Linker-NHS ester (Dye2) | 18174 |
| Dimethyl difluoroluciferin NHS ester (Dye3) | 17665 |
| Monomethyl difluoroluciferin NHS ester (Dye4) | 14665 |
| Difluoro dimethylene Luciferin NHS ester (Dye5) | 11532 |
| Difluoro amide Luciferin NHS ester (Dye6) | 14990 |

The following table (Table 8) provides the data for the various conjugates for six of the dyes of the invention to representative antibodies.

TABLE 8

| Antibody | Dye | Dye to antibody ratio used | Absorption maxima for conjugate | Degree of substitution | Emission maxima for conjugate |
|---|---|---|---|---|---|
| CD4 | Dye1 | 100 | 400 nm | 13.5 | 525 nm |
| CD4 | Dye2 | 60 | 399 nm | 30.4 | 516 nm |
| CD3 | Dye2 | 10 | 399 nm | 5.91 | 516 nm |
| CD45 | Dye2 | 5 | 399 nm | 4.2 | 516 nm |
| CD4 | Dye3 | 100 | 398 nm | 11.4 | 528 nm |
| CD3 | Dye3 | 20 | 398 nm | 4.8 | 528 nm |
| CD45 | Dye3 | 40 | 398 nm | 8.24 | 528 nm |
| CD3 | Dye4 | 30 | 390 nm | 2.89 | 528 nm |
| CD4 | Dye5 | 60 | 390 nm | 20.8 | 527 nm |
| CD3 | Dye5 | 20 | 390 nm | 6.2 | 527 nm |
| CD45 | Dye5 | 15 | 390 nm | 8.31 | 527 nm |
| CD4 | Dye6 | 80 | 382 nm | 27.6 | 517 nm |
| CD3 | Dye6 | 15 | 382 nm | 6.8 | 517 nm |
| CD45 | Dye6 | 10 | 382 nm | 6.8 | 517 nm |
| CD4 | Dye7 | 100 | 391 nm | ND$^a$ | 524 nm |
| CD4 | Dye8 | 100 | 420 nm | ND | 465 nm |
| CD4 | Dye8 | 100 | 420 nm | ND | 465 nm |

$^a$ND means not determined

Example 3

The following example provides method for using the antibody-dye conjugates in flow cytometry.

Flow Analysis

Optimum quantities (determined separately by titration) of various compositions of antibody-dye conjugates of the invention were independently combined with a biological specimen containing whole blood (00.1 mL), incubated for 10-15 minutes, processed using the standard procedure using VersaLyse™ lysing reagent, and analyzed using a flow cytometer. Briefly, the treated biological specimen was combined with the VersaLyse™ reagent/0.2% Formaldehyde (1 mL) for 10 minutes, spinning down the treated specimen, aspirating the supernatant, resuspending the pellet in PBS (2 mL) spinning down the cell suspension and resuspending the pellet in PBS/0.1% formaldehyde (1 mL) for analysis. The lymphocyte population was selected by flow cytometry based on forward and side scatter characteristics. Subpopulations were identified using specific monoclonal antibodies. Fluorescence signals were collected using appropriate band pass filters chosen based on the conjugate's fluorescence emission spectrum.

Similarly, the antibody-Pacific Orange™ conjugates were evaluated. In selected cases, the flow data results of various luciferin derivatives dyes—antibody conjugates were compared with the corresponding antibody-pacific orange dye-conjugates. Following table summarizes these results (Table 9). The conjugates of antibody-fluorescent dyes of the invention showed superior signal/noise values compared to antibody-Pacific Orange conjugate.

TABLE 9

| Conjugate | Signal/Noise values |
|---|---|
| CD4-Pacific Orange | 8.7 |
| CD4-Dye1 | 20.5 |
| CD4-Dye2 | 26.8 |
| CD4-Dye3 | 26.4 |
| CD4-Dye4 | 27.4 |
| CD4-Dye5 | 31.0 |
| CD4-Dye7 | 9.2 |

Figure 4:
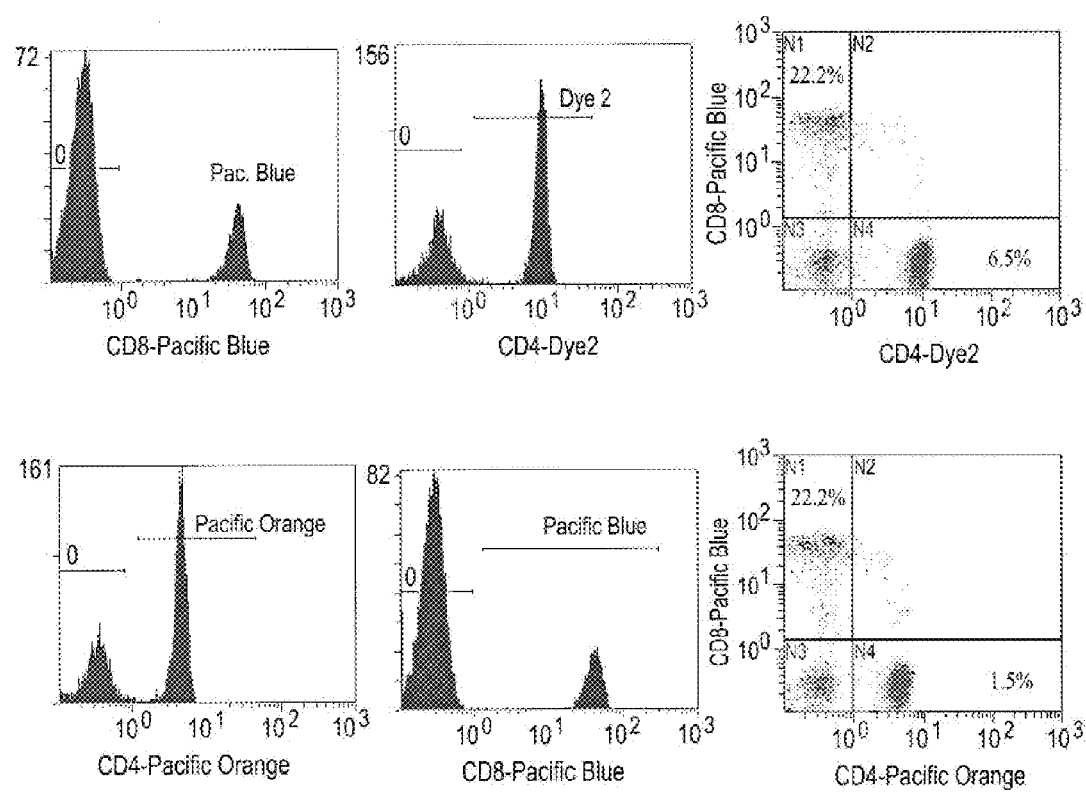
FIG. 4 depicts histograms illustrating the relative performance of CD4-Dye2 conjugate to CD4-Pacific Orange conjugate using two-color flow cytometry.

Two-Color Flow Analysis:

In selected cases, using 405 nm laser line, CD8-Pacific Blue™ dye-conjugate and a CD4-luciferin derivative dye of the invention, a two color flow analysis was similarly performed. The results were compared with the corresponding performance for CD8-Pacific Blue™ dye conjugate and a CD4-Pacific Orange™ dye (Invitrogen Corporation). As shown in FIG. 4, the antibody-Dye2 conjugate showed brighter signal when compared to that of antibody-Pacific Orange™ conjugate.

Multi-Color Flow Analysis:

For one of the dyes (Dye3) of the invention, a ten-color application was also demonstrated on a 3 laser 10 color PMT instrument equipped with a 405 nm laser, 488 nm laser and 635 nm laser. A 550/40 nm band pass filter was used to collect the fluorescence output into the photomultiplier tube. Following antibody reagents were used:

1. CD45 (RA)-FITC
2. CD56-PE
3. CD45(RO)-ECD
4. CD25-PC5
5. CD19-PC7
6. CD3-APC
7. CD27-APCA700
8. CD5-APCCy7
9. CD8-Pacific Blue
10. CD4-Pacific Orange/CD4-Dye3.

Figure 5:
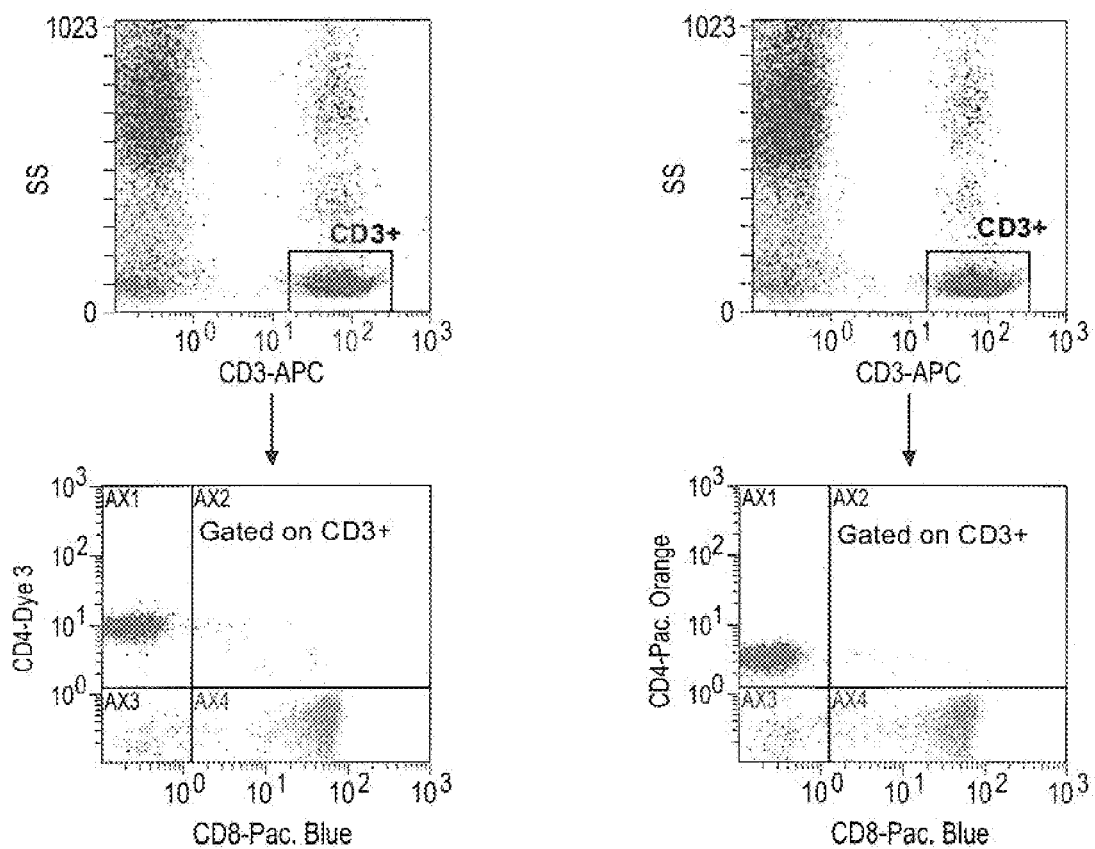
FIG. 5 depicts histograms illustrating the relative performance of CD4-Dye3 to CD4-Pacific Orange conjugate using ten-color flow cytometry.

The histograms shown in FIG. 5 illustrate that in the ten-color flow assay, the CD4-Dye3 conjugate gave a brighter signal when compared to that of CD4-Pacific Orange conjugate.

What is claimed is:

1. A fluorescent dye having the formula:

wherein $X_1$ and $X_2$ are independently S or O;

$Y_1$ and $Y_2$ are independently halogen;

wherein each W is independently H or alkyl;

$Z_1$ is H or alkyl;

wherein $Z_1$ and one of W groups may be absent and, if absent, are replaced with an additional bond between $C_4$ and $C_5$ in ring C;

L is independently a bond or linking group; and

RG is a reactive group.

2. The fluorescent dye of claim 1, wherein the linking group comprises a covalent linkage comprising 1-50 non-hydrogen atoms selected from C, N, O, S, P and halogen atoms and is composed of any combination single, double, triple, or aromatic carbon-carbon bonds, carbon-oxygen bonds, carbon-sulfur bonds, carbon-nitrogen bonds, and nitrogen-nitrogen bonds; and wherein RG comprises a reactive group selected from a group consisting of a carboxylic acid, an activated ester of a carboxylic acid, acid anhydride, acid chloride, acyl azide, an acyl halide, aldehyde, chloroformate, amine, hydroxyl, hydrazine, isocyanate, isothiocyanate, sulfonyl halide, tosyl, maleimide, N-hydroxy-succinimide ester, aziridine, imine, and disulfide.

3. The fluorescent dye of claim 1 or 2, wherein the linking group comprises a formula:

$R_1C(O)R_2$, wherein $R_1$ is a bond or $C_{1-10}$ methylene $(CH_2)n$ attached to the dye, C(O) is a carbonyl group, and $R_2$ is OH or a bond attaching the carbonyl group to the reactive group RG; or $R_1C(O)A_1R_3C(O)R_2$, where $R_1$ is a bond or $C_{1-10}$ methylene, C(O) is a carbonyl group, $A_1$ is either NH, S or O, $R_3$ is an alkenyl $(CH_2)n$, a five or a six membered ring having at least one unsaturated bond, or a combination of $C_{1-10}$ methylene $(CH_2)n$ and a five or six member ring, $R_2$ is OH or a bond attaching the terminal carbonyl group to the reactive group RG.

4. The fluorescent dye of claim 1, wherein RG comprises a carboxylic acid, succinimidyl ester of a carboxylic acid, a hydrazide, an amine, an isothiocyanate, or a maleimide.

5. The fluorescent dye of claim 1, having the formula:

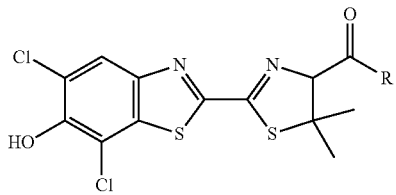

wherein
R represents OH, succinimidoxy, NH(CH$_2$)nCOOH, NH(CH$_2$)$_n$CO-succinimide, or NH(CH$_2$)n-maleimide, wherein n=1-10.

6. The fluorescent dye of claim 1, having the formula:

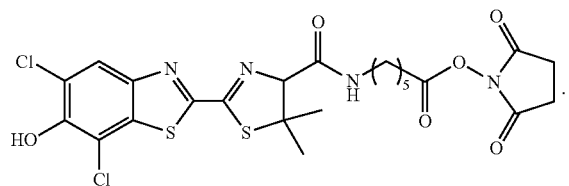

7. The fluorescent dye of claim 1, having the formula:

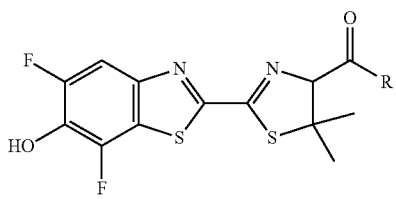

wherein
R represents OH, succinimidoxy, NH(CH$_2$)nCOOH, NH(CH$_2$)$_n$CO-succinimide, or NH(CH$_2$)n-maleimide, wherein n=1-10.

8. The fluorescent dye of claim 1, having the formula:

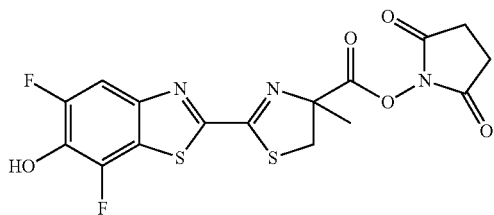

9. The fluorescent dye of claim 1, having the formula:

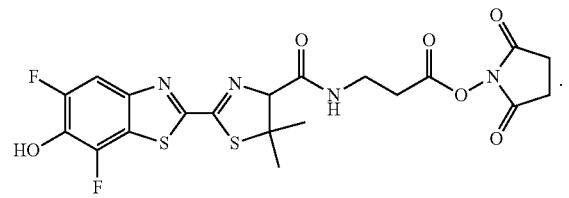 [SMILES: CC1(C)SC(c2nc3cc(F)c(O)c(F)c3s2)=NC1C(=O)NCCC(=O)ON1C(=O)CCC1=O]

10. The fluorescent dye of claim 1, having the formula:

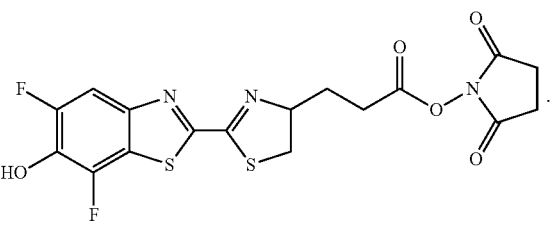 [SMILES: O=C(CCC1CSC(c2nc3cc(F)c(O)c(F)c3s2)=N1)ON1C(=O)CCC1=O]

11. A fluorescent dye having the formula:

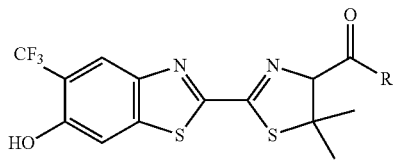

wherein
R represents OH, succinimidoxy, NH(CH$_2$)nCOOH, NH(CH$_2$)$_n$CO-succinimide, or NH(CH$_2$)n-maleimide, wherein n=1-10.

12. A fluorescent dye having the formula:

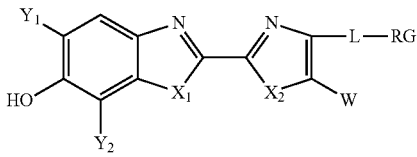

wherein
$X_1$ and $X_2$ are independently S or O;

$Y_1$ and $Y_2$ are independently halogen or one of $Y_1$ or $Y_2$ is H, and the other is a haloalkyl group;

W is H or alkyl;

L is independently a bond or a linking group, wherein the linking group comprises a covalent linkage comprising 1-50 non-hydrogen atoms selected from C, N, O, S, P and halogen atoms and is composed of any combination single, double, triple, or aromatic carbon-carbon bonds, carbon-oxygen bonds, carbon-sulfur bonds, carbon-nitrogen bonds, and nitrogen-nitrogen bonds; and wherein RG is a reactive group selected from a group consisting of a carboxylic acid, an activated ester of a carboxylic acid, acid anhydride, acid chloride, acyl azide, an acyl halide, aldehyde, chloroformate, amine, hydroxyl, hydrazine, isocyanate, isothiocyanate, sulfonyl halide, tosyl, maleimide, N-hydroxy-succinimide ester, aziridine, imine, and disulfide.

13. The fluorescent dye of claim 1, which can be excited with a wavelength from about 340 nm to about 450 nm.

* * * * *